United States Patent
Sill et al.

(10) Patent No.: US 11,478,505 B2
(45) Date of Patent: Oct. 25, 2022

(54) COMPOSITIONS OF IXABEPILONE

(71) Applicant: R-Pharm US Operating LLC, Lawrenceville, NJ (US)

(72) Inventors: Kevin N. Sill, Tampa, FL (US); Bradford T. Sullivan, Clearwater, FL (US)

(73) Assignee: R-Pharm US Operating LLC, Lawrenceville, NJ (US)

(*) Notice: Subject to any disclaimer, the term of this patent is extended or adjusted under 35 U.S.C. 154(b) by 31 days.

(21) Appl. No.: 17/144,405

(22) Filed: Jan. 8, 2021

(65) Prior Publication Data

US 2021/0213044 A1 Jul. 15, 2021

Related U.S. Application Data

(60) Provisional application No. 62/959,495, filed on Jan. 10, 2020.

(51) Int. Cl.
| | | |
|---|---|---|
| A61K 31/785 | (2006.01) | |
| A61K 9/19 | (2006.01) | |
| A61K 31/427 | (2006.01) | |
| A61K 45/06 | (2006.01) | |
| A61K 47/18 | (2017.01) | |

(52) U.S. Cl.
CPC .......... *A61K 31/785* (2013.01); *A61K 9/19* (2013.01); *A61K 31/427* (2013.01); *A61K 45/06* (2013.01); *A61K 47/18* (2013.01)

(58) Field of Classification Search
CPC ...... A61K 31/785; A61K 9/19; A61K 31/427; A61K 45/06; A61K 47/18
See application file for complete search history.

(56) References Cited

U.S. PATENT DOCUMENTS

| | | | |
|---|---|---|---|
| 2,671,772 A | 3/1954 | MacDonald | |
| 8,980,326 B2 | 3/2015 | Sill et al. | |
| 9,078,930 B2 | 7/2015 | Sill et al. | |
| 10,836,869 B1 | 11/2020 | Sill et al. | |
| 10,918,619 B1 | 2/2021 | Sill et al. | |
| 11,286,344 B2 | 3/2022 | Sill et al. | |
| 2008/0274173 A1 | 11/2008 | Sill et al. | |
| 2014/0271885 A1* | 9/2014 | Sill ................. | A61K 31/704 424/490 |
| 2018/0228796 A1 | 8/2018 | Sill | |
| 2021/0214496 A1 | 7/2021 | Sill et al. | |

FOREIGN PATENT DOCUMENTS

| | | |
|---|---|---|
| CN | 102935062 A | 2/2013 |
| EP | 2660255 | 11/2013 |
| EP | 3266456 | 1/2018 |
| WO | 2004017940 | 3/2004 |
| WO | 2005117833 | 12/2005 |
| WO | 2008134731 | 11/2008 |

OTHER PUBLICATIONS

David Heusmann, et al, A Head-to-Head Comparison of Poly(sarcosine) and Poly(ethylene glycol) in Peptidic, Amphiphilic Block Copolymers, 67 Polymer 240 (Year: 2015).*
Adams, et.al. "Amphiphilic Block Copolymers for Drug Delivery" Journal of Pharmaceutical Sciences, 92(7)1343-1355(2003).
Armstrong, "The occurrence, induction, specificity and potential effect of antibodies against poly(ethylene glycol)," PEGylated Protein Drugs: Basic Science and Clinical ApplicAtions, Birkhiiuser Verlag/Switzerland, pp. 147-168 (2009) (22 pages).
Arnould, et al., "Meganuclease fusion proteins and their use in targeted integration of transforming DNA," Caplus, 2003:757845 (2020) (2 pages).
Bae et al., "Oil-encapsulating PEO-PPO-PEO/PEG shell cross-linked nanocapsules for target-specific delivery of paclitaxel," Biomacromolecules, 8(2):650-656 (2007).
Birke, et al., "Polypeptoid-block-polypeptide Copolymers: Synthesis, Characterization, and Application of Amphiphilic Block Copolypept(o)ides in Drug Formulations and Miniemulsion Techniques," Biomacromolecules, 15(2):548-557 (2014).
Birke, et al., "Polysarcosine-containing copolymers: Synthesis, characterization, self-assembly, and applications," Progress in Polymer Science, 81: 163-208 (2018).
Chan, et al., "Polypeptoid polymers: Synthesis, characterization, and properties." Biopolymers, 109(1):e23070 (2018).
Chen, et al., "GoldNanoparticles Coated With Polysarcosme Brushes to Enhance Their Colloidal Stability and Circulation Time in Vivo," Journal of Colloid and Interface Science, 483:201-210 (2016).
Ferrari, "Cancer Nanotechnology: Opportunities and Challenges," Nature Reviews, 5(3):161-171 (2005).
Fetsch et al., "Polypeptoids from N-Substituted Glycine N-Carboxvanhydrides: Hydrophilic, Hydrophobic, and Amphiphilic Polymers with Poisson Distribution," Macromolecules, 44:6746-6758 (2011).
Ford, et al., "Nucleic acids and their encoded polypeptides from human bone marrow", Caplus, 2001:661557 (2001) 1 page.
Fournier, et al. "A Novel One-Step Drug-Loading Procedure for Water-Soluble Amphiphilic Nanocarriers," Pharmaceutical Research, 21(6):962-968 (2004).
Hamaguchi, et al., "NK105, a Paclitaxel-Incorporating Micellar Nanoparticle Formulation, Can Extend in Vivo Antitumour Activity and Reduce the Neurotoxicity of Paclitaxel," British Journal of Cancer 92: 1240-1246 (2005).

(Continued)

*Primary Examiner* — Sean M Basquill
(74) *Attorney, Agent, or Firm* — Hamilton, Brook, Smith & Reynolds, P.C.

(57) ABSTRACT

Provided herein are compositions comprising ixabepilone, or a pharmaceutically acceptable salt thereof, and a copolymer represented by formula I:

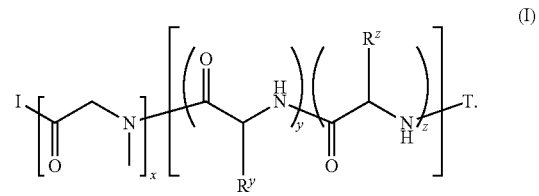

Also provided are methods of treating cancer using the compositions described herein, and methods of preparing the compositions.

23 Claims, 5 Drawing Sheets

(56) References Cited

OTHER PUBLICATIONS

Heusmann, "A head-to-head comparison of poly(sarcosine) and poly(ethyleneglycol) in peptidic, amphiphilic block copolymers," Polymer 67:240e248 (2015).

Hu, et al., "Polysarcosine as an Alternative to PEG for Therapeutic Protein Conjugation," Bioconjugate Chemistry, 29(7):2232-2238 (2018).

Keck, et al., "Computer method and apparatus for classifying objects such as protein sequences and its application with cyclic peptides osteogenic modulators of bone morphogenetic protine-7," Caplus, 2004:485563 (2020) (2 pages).

Nishiyama, "Nanomedicine: Nanocarriers Shape Up for Long Life, Nature Nanotechnology," 2(4):203-204 (2007).

Rios-Doria, et al., "A Versatile Polymer Micelle Drug Delivery System for Encapsulation and In Vivo Stabilization of Hydrophobic Anticancer Drugs," Journal of Drug Delivery, 2012 (8 pages) (2012).

Sill, et al., "Synthesis and Characterization of Micelle-Forming PEG-Poly(Amino Acid) Copolymers With Iron-Hydroxamate Cross-Linkable Blocks for Encapsulation and Release of Hydrophobic Drugs," Biomacromolecules, 18(6):1874-1884 (2017).

Sparreboom, et al., "Comparative Preclinical and Clinical Pharmacokinetics of a Cremophor-Free, Nanoparticle Albumin-Bound Paclitaxel (ABI-007) and Paclitaxel Formulated in Cremophor (Taxol)." Clinical Cancer Research, 11(11):4136-4143 (2005).

Torchilin, "Structure and Design of Polymeric Surfactant-Based Drug Delivery Systems," 73(2-3):137-172 (2001).

Varias, et al., "Poly(sarcosine)-Based Nano-Objects with Multi-Protease Resistance by Aqueous Photoinitiated Polymerization-Induced Self-Assembly," Biomacromolecules, 19(11):4453-4462 (2018).

Viricel, et al., "Monodisperse polysarcosine-based highly-loaded antibody-drug conjugates" Chemical Science, 10(14):4048-4053 (2019).

Weber, et al., "Polysarcosine-Based Lipids: From Lipopolypeptoid Micelles to Stealth-Like Lipids in Langmuir Blodgett Monolayers," Polymers, 8(12):427 (2016) (14 pages).

Weber, et al., "Solution Properties of Polysarcosine: From Absolute and Relative Molar Mass Determinations to Complement Activation," Macromolecules, 51:2653-2661 (2018).

Notification of Transmittal of The International Search Report and the Written Opinion of the International Searching Authority, or the Declaration for International Application No. PCT/US2021/012614, "Compositions of Ixabepilone", dated Apr. 28, 2021.

Tkaczuk, K, et al., "Ixabepilone as Monotherapy or in Combination with Capecitabine for the Treatment of Advanced Breast Cancer", Breast Cancer: Basic and Clinical Research, vol. 5, Jan. 13, 2011, pp. 1-14.

* cited by examiner

COMPOSITIONS OF IXABEPILONE

RELATED APPLICATION

This application claims the benefit of U.S. Provisional Application No. 62/959,495, filed on Jan. 10, 2020. The entire teachings of this application are incorporated herein by reference.

COMMON OWNERSHIP UNDER JOINT RESEARCH AGREEMENT 35 U.S.C. 102(c)

The subject matter disclosed in this application was developed, and the claimed invention was made by, or on behalf of, one or more parties to a joint Research Agreement that was in effect on or before the effective filing date of the claimed invention. The parties to the Joint Research Agreement are R-Pharm US Operating LLC and Tyndall Formulation Services LLC.

BACKGROUND

Ixabepilone is marketed under the brand name IXEMPRA® for the treatment of metastatic or locally advanced breast cancer. Ixabepilone is difficult to formulate due to very low solubility in aqueous media, propensity to degrade in aqueous media, sensitivity to low pH and light, and poor wetting properties. Currently, IXEMPRA® is provided as a kit with two vials. One vial contains ixabepilone as a lyophilized powder, and the other vial contains 52.8% (weight/volume, w/v) CREMOPHOR® EL and 39.8% (w/v) dehydrated alcohol.

CREMOPHOR® EL is associated with several infusion-related side effects, including bronchospasm, hypotension, peripheral neuropathy and anaphylactic reactions. The side effects associated with CREMOPHOR® EL necessitate premedication with $H_1$ and $H_2$ antagonists and prolonged infusion times to reduce hypersensitivity reactions for CREMOPHOR® EL-containing formulations. In addition, non-standard intravenous tubing must be utilized when administering IXEMPRA®, as CREMOPHOR® EL extracts the plasticizer (di-(2-ethylhexyl)phthalate (DEHP)) from polyvinyl chloride.

Accordingly, there is a need for alternative compositions of ixabepilone, particularly those that do not require reconstitution in CREMOPHOR® EL.

SUMMARY

Provided herein is a composition comprising ixabepilone, or a pharmaceutically acceptable salt thereof, and a copolymer represented by formula I:

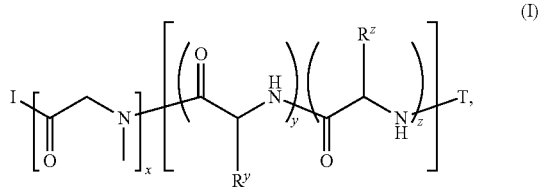

wherein:
I is an initiating group;
T is a terminal group;
$R^y$ and $R^z$ are each independently an amino acid side chain, wherein $R^y$, taken together with the amino acid backbone to which it is attached forms a D-amino acid and $R^z$, taken together with the amino acid backbone to which it is attached forms an L-amino acid;
x is an integer from 125 to 350;
y is an integer from 5 to 35; and
z is an integer from 5 to 35.

Also provided herein is a composition comprising about 10% ixabepilone by weight; about 45% copolymer by weight; and about 45% glycine by weight, wherein the copolymer is represented by formula II:

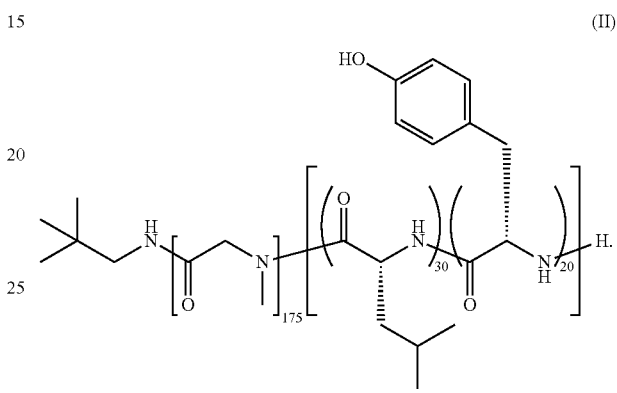

Also provided herein is a unit dose form of a composition comprising about 20 mg ixabepilone; about 180 mg copolymer; and about 180 mg glycine, wherein the copolymer is represented by formula II.

Also provided herein is a method for treating cancer in a subject in need thereof, comprising administering to the subject an effective amount of a composition or a unit dose form described herein. Also provided is a composition described herein for use in treating cancer. Also provided is use of a composition described herein for the manufacture of a medicament for the treatment of cancer.

Also provided herein is a method for treating metastatic or locally advanced breast cancer in a human who has failed a prior treatment comprising an anthracycline and a taxane, the method comprising administering to the human an effective amount of a composition or a unit dose form described herein; and capecitabine. Also provided is a composition described herein for use in treating metastatic or locally advanced breast cancer in a human who has failed a prior treatment comprising an anthracycline and a taxane. Also provided is use of a composition described herein for the manufacture of a medicament for the treatment of metastatic or locally advanced breast cancer in a human who has failed a prior treatment comprising an anthracycline and a taxane.

Also provided herein is a method for treating metastatic or locally advanced breast cancer in a human who has failed a prior treatment comprising an anthracycline, a taxane and capecitabine, the method comprising administering to the human an effective amount of a composition or a unit dose form described herein. Also provided is a composition described herein for use in treating metastatic or locally advanced breast cancer in a human who has failed a prior treatment comprising an anthracycline, a taxane and capecitabine. Also provided is use of a composition described herein for the manufacture of a medicament for the treatment of metastatic or locally advanced breast cancer in a human who has failed a prior treatment comprising an anthracycline, a taxane and capecitabine.

Also provided herein is a method of preparing a composition or a unit dose form described herein, comprising dissolving ixabepilone, or a pharmaceutically acceptable salt thereof, a copolymer described herein and, optionally, a cryoprotectant in aqueous tert-butanol, thereby forming a mixed solution; and lyophilizing the mixed solution, thereby preparing the composition or unit dose form.

BRIEF DESCRIPTION OF THE DRAWINGS

The foregoing will be apparent from the following more particular description of example embodiments.

DETAILED DESCRIPTION

Figure 1:
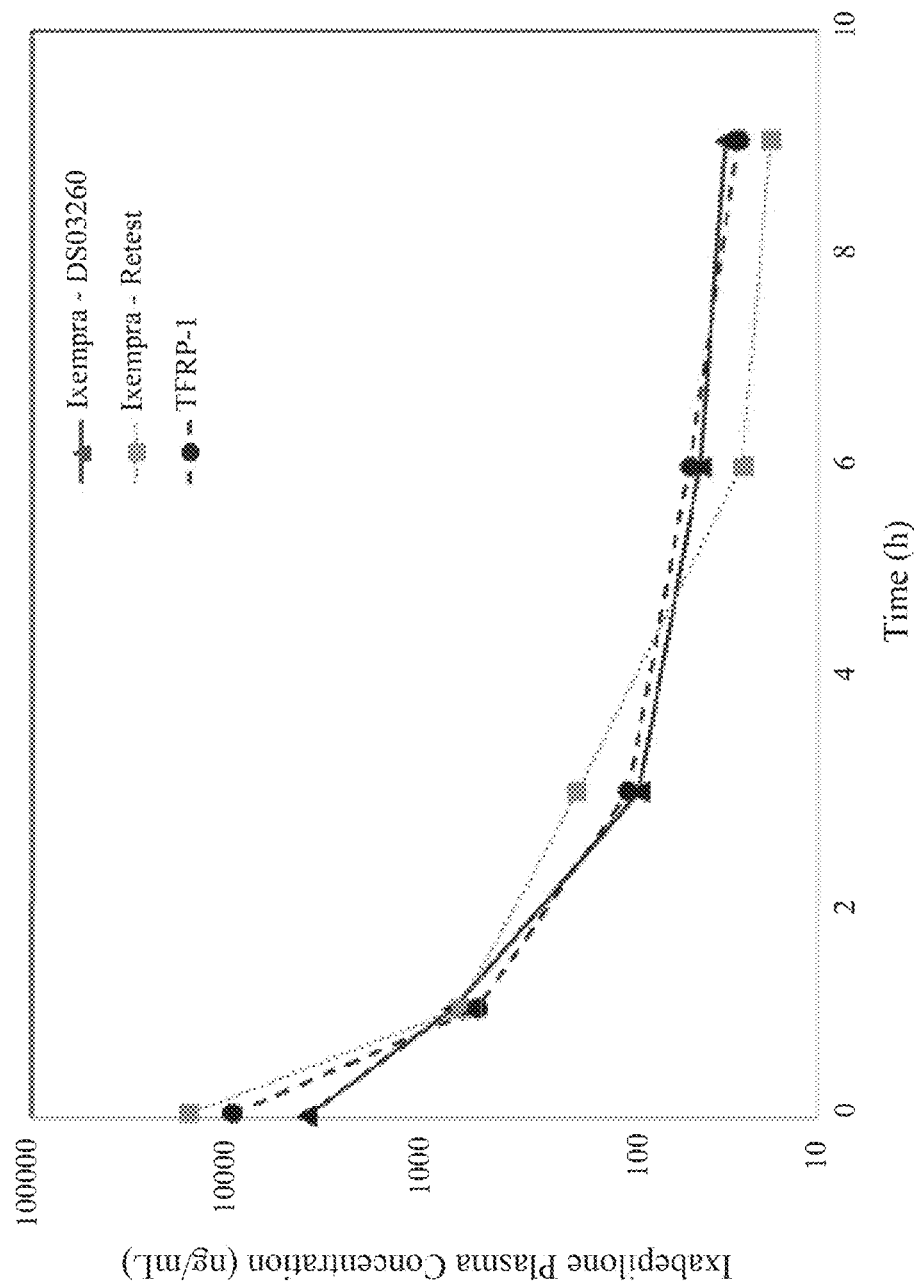
FIG. 1 is a graph of ixabepilone plasma concentration (ng/mL) versus time (h), and shows the pharmacokinetic profile of TFRP-1 versus IXEMPRA®.

A description of example embodiments follows.

Definitions

For purposes of this invention, the chemical elements are identified in accordance with the Periodic Table of the Elements, CRC Handbook of Chemistry and Physics, $100^{th}$ Ed. Additionally, general principles of organic chemistry are described in Sorrell, T. *Organic Chemistry, $2^{nd}$* Ed., Sausalito, University Science Books, 2005; and Smith, M. B. *March's Advanced Organic Chemistry: Reactions, Mechanisms, and Structure, $7^{th}$* Ed., New York, J. John Wiley & Sons, 2001, the entire contents of which are hereby incorporated by reference.

The terms "a," "an," "the" and similar terms used in the context of the present invention (especially in the context of the claims) are to be construed to cover both the singular and plural unless otherwise indicated or clearly contradicted by the context.

The term "about," when referring to a measurable value such as an amount, a temporal duration, and the like, refers to variations of ±20% or, in some instances, ±10% or, in some instances, ±5% or, in some instances, ±1% or, in some instances, ±0.1% from the specified value, as such variations are appropriate to perform the present inventions.

As used herein, the term "multiblock poly(amino acid) copolymer" refers to a polymer comprising two or more poly(amino acid) blocks. One or more of the amino acid blocks may be "mixed blocks," meaning that the block contains a mixture of different amino acid monomers. As is typical in the art, the monomer repeat unit is defined by parentheses depicted around the repeating monomer unit. The number (or letter representing a numeral or numerical range) at the lower right of the parentheses represents the monomer repeat unit. In the case of a mixed block, multiple monomers comprise a single, continuous block. It will be understood that brackets will define a portion or block. For example, one block may consist of four individual monomers, each defined by its own individual set of parentheses and monomer repeat units. All four sets of parentheses will be enclosed by a set of square brackets, denoting that all four of these monomers combine in random, or near random, order to form the mixed block. For clarity, the randomly mixed block of [BCADDCBADABCDABC] would be represented in shorthand by $[(A)_4(B)_4(C)_4(D)_4]$. In the case where a block contains a single monomer (i.e., a homopolymeric block), the block may be denoted solely by square brackets, and the number (or letter representing a numeral or numerical range) at the lower right of the square brackets will represent the monomer repeat unit of that block.

The monomer repeat unit is a numerical value representing the average number of monomer units in the indicated polymer chain. For example, a polymer represented by $(A)_{10}$ corresponds to a polymer consisting of an average of ten "A" monomer units linked together. One of ordinary skill in the art will recognize that the number 10 in this example represents a distribution of numbers with an average of 10. The breadth of this distribution is represented by the polydispersity index (PDI), which is the quotient of weight average molecular weight ($M_w$) divided by number average molecular weight ($M_n$). A PDI of 1.0 corresponds to a polymer wherein each chain length is exactly the same, as in a protein, for example. A PDI of 2.0 corresponds to a polymer wherein the chain lengths have a Gaussian distribution. PDI can be calculated by size exclusion software, such as ASTRA®. In some embodiments, the polymers described herein have a PDI of less than 2.0, less than 1.5, less than 1.2 or about 1.1. Polymers of the present invention typically possess a PDI of less than 1.2.

As used herein, the term "poly(amino acid)" refers to a covalently-linked chain of amino acids. Examples of poly (amino acids) include poly(leucine-co-tyrosine), and poly (phenylalanine-co-tyrosine).

As used herein, the term "amino acid" refers to a molecule containing an amino acid backbone covalently bonded to an amino acid side chain. It will be understood that "amino acid," used herein, encompasses free amino acids, for example, that can be represented by the following formula: HO—C(O)C(R)(H)N(H)—H, or a salt thereof, wherein —C(O)C(H)N(H)— is the amino acid backbone and R is the amino acid side chain. Substitutions in the amino acid, such as a substitutions of the N(H), which include proline (e.g., N(—C(H)$_2$—C(H)$_2$—C(H)$_2$—)) and sarcosine (e.g., N(Me)) are encompassed in "amino acid". "Amino acid" also encompasses amino acids covalently bound via the terminal carbonyl carbon of their backbones to an entity other than —OH, or a salt form thereof, and/or covalently bound via the terminal nitrogen of their backbones to an entity other than hydrogen as, for example, in embodiments of copolymers described herein. When an amino acid is designated by name, the name may refer to the referenced amino acid in free form or covalently bound via the terminal carbonyl carbon and/or the terminal nitrogen of its backbone to the other entity(ies), as context indicates. For example, "glycine" may be used to refer to HO$_2$CCH$_2$NH$_2$, or a salt thereof, and/or —C(O)CH$_2$N(H)—, wherein at least one "-" represents a covalent bond between the amino acid backbone of glycine and the other entity(ies). A person skilled in the art will be able to determine from the context if the amino acid is present in free form or covalently bound via the terminal carbonyl carbon and/or the terminal nitrogen of its backbone to the other entity(ies) as, for example, in embodiments of copolymers described herein. "Amino acid" includes both naturally-occurring amino acids and non-naturally-occurring amino acids. "Amino acid" also includes canonical amino acids, non-canonical amino acids, L-amino acids and D-amino acids. In one embodiment, an amino acid is a naturally-occurring amino acid.

"Amino acid backbone," as used herein, refers to the following common set of atoms that make up amino acids: —C(O)C(H)N(H)—. Amino acid side chains are attached to the amino acid backbone at the alpha carbon of the backbone. The alpha carbon of an amino acid backbone is indicated with a *: —C(O)C*(H)N(H)—.

"Amino acid side chain," as used herein, refers to the substituent covalently bonded to the alpha carbon atom of an amino acid backbone. Examples of amino acid side chains include hydrogen (as in glycine, for example), methyl (as in alanine, for example), —C(H)(CH$_3$)(CH$_2$CH$_3$) (as in isoleucine, for example), —C(H)$_2$(C(H)(CH$_3$)$_2$) (as in leucine, for example), —CH$_2$CH$_2$SCH$_3$ (as in methionine, for example), —CH$_2$C$_6$H$_5$ (as in phenylalanine, for example), —CH$_2$-(1H-indol-3-yl) (as in tryptophan, for example), p-methoxybenzyl (as in tyrosine, for example), —C(H)(CH$_3$)$_2$ (as in valine, for example), —CH$_2$CH$_2$CH$_2$— (as in proline, for example), —CH$_2$C(O)NH$_2$ (as in asparagine, for example), —CH$_2$CH$_2$C(O)NH$_2$ (as in glutamine, for example) and —(CH$_2$)$_2$CO$_2$CH$_2$C$_6$H$_5$ (as in γ-benzyl-glutamate, for example). It will be understood, therefore, that when R$^y$ or R$^z$, taken together with the amino acid backbone to which it is attached, forms an amino acid selected from glycine, alanine, isoleucine, leucine, methionine, phenylalanine, tryptophan, tyrosine, valine, proline, asparagine, glutamine or γ-benzylglutamate. R$^y$ or R$^z$ is hydrogen, methyl, —C(H)(CH$_3$)(CH$_2$CH$_3$), —C(H)$_2$(C(H)(CH$_3$)$_2$), —CH$_2$CH$_2$SCH$_3$, —CH$_2$C$_6$H$_5$, —CH$_2$-(1H-indol-3-yl), p-methoxybenzyl, —C(H)(CH$_3$)$_2$, —CH$_2$CH$_2$CH$_2$—, —CH$_2$C(O)NH$_2$, —CH$_2$CH$_2$C(O)NH$_2$ or —(CH$_2$)$_2$CO$_2$CH$_2$C$_6$H$_5$, respectively.

As used herein, the term "naturally-occurring amino acid" means a compound represented by the formula —N(H)—C(H)(R)—C(O)—, wherein R is the amino acid side chain of a naturally-occurring amino acid (e.g., naturally occurring in proteins, naturally occurring in nature), such as an amino acid listed or named in the Table of Selected Naturally Occurring Amino Acids below. "Naturally-occurring amino acid" includes both the D- and L-configurations of an amino acid represented by the formula —N(H)—C(H)(R)—C(O)—, wherein R is the amino acid side chain of a naturally-occurring amino acid. When an amino acid is named or depicted by structure without indicating the stereochemistry and has at least one chiral center, it is to be understood that the name or structure encompasses a single enantiomer or diastereomer, a racemic or diastereomeric mixture of the enantiomer or diastereomer(s) and mixtures enriched in one enantiomer or diastereomer relative to its corresponding enantiomer or other diastereomer(s).

Table of Selected Naturally Occurring Amino Acids

| | Amino acid | Three letter code | One letter code |
|---|---|---|---|
| Hydrophobic | glycine | Gly | G |
| | alanine | Ala | A |
| | isoleucine | Ile | I |
| | leucine | Leu | L |
| | methionine | Met | M |
| | phenylalanine | Phe | F |
| | proline | Pro | P |
| | tryptophan | Trp | W |
| | valine | Val | V |
| Hydrophilic | asparagine | Asn | N |
| | cysteine | Cys | C |
| | glutamine | Gln | Q |
| | serine | Ser | S |
| | threonine | Thr | T |
| | tyrosine | Tyr | Y |
| | glutamic acid | Glu | E |
| | arginine | Arg | R |
| | aspartic acid | Asp | D |
| | histidine | His | H |
| | lysine | Lys | K |
| | sarcosine | Sar | |

"Non-natural amino acid," as used herein, refers to an amino acid that is not a naturally-occurring amino acid. Examples of non-natural amino acids include γ-benzyl-glutamate, homoserine, ornithine and thyroxine.

"D-amino acid," as used herein, refers to an amino acid in the D-configuration.

"L-amino acid," as used herein, refers to an amino acid in the L-configuration.

Tacticity can be used to describe the stereochemistry of adjacent chiral centers in a poly(amino acid). A poly(amino acid) consisting of amino acids of a single configuration (e.g., all L-amino acids, all D-amino acids) is referred to as "isotactic." A poly(amino acid) consisting of a random incorporation of D- and L-amino acid monomers is referred to as "atactic." A poly(amino acid) consisting of amino acid monomers with alternating stereochemistry (e.g., . . . DLD-LDL . . . ) is referred to as "syndiotactic." Polymer tacticity is described in more detail in Odian, G. *Principles of Polymerization*, 4$^{th}$ Ed., New York, John Wiley & Sons, 1991, the entire contents of which are incorporated herein by reference. In some embodiments, a copolymer described herein is isotactic. In some embodiments, the copolymer is atactic. In some embodiments, the copolymer is syndiotactic.

"Initiating group," as used herein, refers to a radical of a polymerization initiator. Examples of initiating groups include optionally substituted benzylamino (e.g., benzylamino, p-methylbenzylamino, p-methoxybenzylamino), optionally substituted aliphatic amino (e.g., neopentylamino, n-hexylamino, benzylamino, p-methylbenzylamino, p-methoxybenzylamino), optionally substituted silylamino, poly(amino acid) polymers (e.g., poly(sarcosine)), poly(ethylene glycol) polymers, poly(N-isopropylacrylamide) polymers, poly(acrylamide) polymers, poly(2-oxazoline) polymers, poly(ethylenimine), poly(acrylic acid) polymers, poly(methacrylate) polymers, poly(vinyl alcohol) polymers, poly(vinylpyrrolidone) polymers, and their corresponding salts (e.g., amino salts). In some embodiments, the initiating group is benzylamino, p-methylbenzylamino, p-methoxybenzylamino, n-hexylamino or neopentylamino (e.g., neopentylamino).

"Polymerization initiator," as used herein, refers to a compound that reacts with, or whose anion or free base form reacts with, a monomer (e.g., an amino acid) in a manner that results in polymerization of the monomer. In some embodiments, the polymerization initiator is an amine, alcohol or thiol (e.g., an amine). Examples of polymerization initiators include optionally substituted benzylamines (e.g., benzylamine, p-methylbenzylamine, p-methoxybenzylamine), optionally substituted aliphatic amines (e.g., neopentylamine n-hexylamine, benzylamino, p-methylbenzylamino, p-methoxybenzylamino), optionally substituted silylamines, poly(amino acid) polymers (e.g., poly(sarcosine)), poly(ethylene glycol) polymers, poly(N-isopropylacrylamide) polymers, poly(acrylamide) polymers, poly(2-oxazoline) polymers, poly(ethylenimine), poly(acrylic acid) polymers, poly(methacrylate) polymers, poly(vinyl alcohol) polymers, poly(vinylpyrrolidone) polymers, and their corresponding salts (e.g., amine salts). In some embodiments, the polymerization initiator is benzylamine, p-methylbenzylamine, p-methoxybenzylamine, n-hexylamine or neopentylamine (e.g., neopentylamine).

"Terminal group," as used herein, refers to a radical of a living polymer chain-end or a capping group (e.g., a detectable label).

"Living polymer chain-end," as used herein, refers to the terminus of a polymer resulting from the polymerization reaction used to produce the polymer. Typically, when T is a living polymer chain-end, the polymer retains the ability to react, for example, with additional monomer or an electrophile, to form a polymer having a non-living polymer chain-end, such as a capping group or detectable label.

"Capping group," as used herein, refers to a terminal group that is not a living polymer chain-end. The capping group is covalently linked to the amino terminus of a polymer described herein, and may be useful to inhibit or prevent intramolecular cyclization or further intermolecular polymerization, to enhance the hydrophilicity or hydrophobicity of the polymer, to prevent degradation of the polymer or to provide a combination of these properties. Examples of capping groups include acyl groups, such as —C(O)($C_1$-$C_{25}$)aliphatic (e.g., acetyl). Further examples of capping groups include optionally substituted aliphatic, such as optionally substituted ($C_1$-$C_{25}$)aliphatic.

"Detectable label," as used herein, refers to a radical of a molecule that, upon incorporation into a polymer described herein, makes the polymer directly or indirectly detectable. Typically, detectable labels that are capable of direct detection include a signal-generating group, such as a radionuclide (e.g., $^{32}P$, $^{33}P$, $^{35}S$ or $^{14}C$), a mass tag or fluorescent group. Detectable labels that are indirectly detectable usually require the presence of a second molecule to produce a detectable signal. Such is the case, for example, with biotin or protein antigens, which typically require the presence of one or more proteins to be detected, and with fluorescent groups that transfer energy to another molecule that is detected in a process of nonradiative fluorescent resonance energy transfer (FRET).

"Hydrophobic block," as used herein, refers to a block of a polymer (e.g., a copolymer, such as a multiblock copolymer) that repels water. In some embodiments, a hydrophobic block comprises a hydrophobic amino acid (e.g., a hydrophobic amino acid from the Table of Selected Naturally Occurring Amino Acids, such as leucine) and a hydrogen bonding amino acid (e.g., a hydrophilic amino acid from the Table of Selected Naturally Occurring Amino Acids, such as tyrosine).

"Aliphatic," as used herein, refers to a non-aromatic, branched, unbranched or cyclic, hydrocarbon radical having the specified number of carbon atoms. Thus, "($C_1$-$C_{10}$) aliphatic" refers to an aliphatic radical having from one to 10 carbon atoms. In some embodiments, "aliphatic" has from 1 to 25 carbon atoms. In some embodiments, "aliphatic" has from 1 to 15 carbon atoms. In some embodiments, "aliphatic" has from 1 to 10 carbon atoms. In some embodiments, "aliphatic" has from 1 to 6 carbon atoms. "Aliphatic" can be saturated or contain one or more units of unsaturation. Examples of aliphatic include alkyl, alkenyl and alkynyl, as well as combinations thereof.

"Alkyl," as used herein, refers to a saturated, branched or unbranched, aliphatic, hydrocarbon radical having the specified number of carbon atoms. Thus, "($C_1$-$C_{10}$)alkyl" refers to a radical having from one to 10 carbon atoms in a linear or branched arrangement. In some embodiments, "alkyl" has from 1 to 25 carbon atoms. In some embodiments, "alkyl" has from 1 to 15 carbon atoms. In some embodiments, "alkyl" has from 1 to 10 carbon atoms. In some embodiments, "alkyl" has from 1 to 6 carbon atoms. Alkyl includes methyl, ethyl, propyl, isopropyl, butyl, pentyl, neopentyl, hexyl, etc."

Alkenyl," as used herein, refers to a branched or unbranched, aliphatic, hydrocarbon radical having the specified number of carbon atoms and at least one carbon-carbon double bonds. Thus, "($C_1$-$C_{10}$)alkenyl" refers to a radical having from one to 10 carbon atoms in a linear or branched arrangement and at least one carbon-carbon double bond. In some embodiments, "alkenyl" has from 1 to 25 carbon atoms. In some embodiments, "alkenyl" has from 1 to 15 carbon atoms. In some embodiments, "alkenyl" has from 1 to 10 carbon atoms. In some embodiments, "alkenyl" has from 1 to 6 carbon atoms. Alkenyl includes ethenyl, 2-propenyl, 1-propenyl, 2-methyl-1-propenyl, 1-butenyl, 2-butenyl, 1-pentenyl, 2-pentenyl, 3-pentenyl, allyl, 1, 3-butadienyl, 1, 3-dipentenyl, 1,4-dipentenyl, 1-hexenyl, 1,3-hexenyl, 1,4-hexenyl, 1,3,5-trihexenyl, 2,4-dihexenyl, etc.

"Alkynyl," as used herein, refers to a branched or unbranched, aliphatic, hydrocarbon radical having the specified number of carbon atoms and at least one carbon-carbon triple bond. Thus, "($C_1$-$C_{10}$)alkynyl" refers to a radical having from one to 10 carbon atoms in a linear or branched arrangement and at least one carbon-carbon triple bond. In some embodiments, "alkynyl" has from 1 to 25 carbon atoms. In some embodiments, "alkynyl" has from 1 to 15 carbon atoms. In some embodiments, "alkynyl" has from 1 to 10 carbon atoms. In some embodiments, "alkynyl" has from 1 to 6 carbon atoms. Alkynyl includes ethynyl, 1-propynyl, 2-propynyl, 1-butynyl, 2-butynyl, 2-methyl-1-butynyl, 1-pentynyl, 2-pentynyl, 3-pentynyl, 3-methyl-1-pentynyl, 2-methyl-1-pentynyl, 1-hexynyl, 2-hexynyl, 3-hexynyl, etc.

"Amino," as used herein, refers to —NR'R" wherein R' and R" are independently selected from hydrogen and optionally substituted aliphatic, e.g., ($C_1$-$C_{10}$)aliphatic. Examples of amino include —NH$_2$, benzylamino, p-methylbenzylamino, p-methoxybenzylamino, hexylamino and neopentylamino.

"Halogen" and "halo" are used interchangeably herein, and each refers to fluorine, chlorine, bromine, or iodine. In some embodiments, halogen is selected from fluoro, chloro or bromo.

"Hydroxyl" means —OH.

"Alkoxy," as used herein, refers to an alkyl radical attached through an oxygen linking atom, wherein "alkyl" is as described herein.

"Thio" means —SH.

"Thioalkoxy," as used herein, refers to an alkyl radical attached through a sulfur linking atom, wherein "alkyl" is as described herein.

It is understood that substituents on the copolymers described herein can be selected by one of ordinary skill in the art to provide compounds that are chemically stable and that can be readily synthesized by techniques known in the art, as well as those methods set forth below. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

When a compound or group described herein (e.g., a copolymer, I, T) is "substituted," one or more hydrogen atoms of the substituted compound or group is replaced with a suitable substituent. An "optionally substituted" compound or group can be substituted, as that term is described herein, or unsubstituted. Unless otherwise indicated, when a compound or group is substituted, the compound or group can have a suitable substituent at each substitutable position of the compound or group, and when more than one substitutable position in any given compound or structure is substituted, each substituent can be the same or different (e.g., each substituent can be independently selected). In some embodiments, an optionally substituted compound or group is substituted with 0-5 independently selected suitable substituents, e.g., 0-3, 0, 1, 2, 3, 4 or 5 independently selected suitable substituents.

When a compound or group described herein (e.g., a copolymer, I, T) is "substituted," one or more hydrogen atoms of the substituted compound or group is replaced with a suitable substituent. An "optionally substituted" compound or group can be substituted, as that term is described herein, or unsubstituted. Unless otherwise indicated, when a compound or group is substituted, the compound or group can have a suitable substituent at each substitutable position of the compound or group, and when more than one substitutable position in any given compound or structure is substituted, each substituent can be the same or different (e.g., each substituent can be independently selected).

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ C(O)NR^\circ)_2$; $-N(R^\circ)C(S)NR^\circ)_2$; $-(CH_2)_{0-4}N(R^\circ C(O)OR^\circ$; $-N(R^\circ)N(R^\circ)C(O)R^\circ$; $-N(R^\circ)N(R^\circ C(O)NR^\circ)_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$; $-SC(S)SR^\circ$; $-(CH_2)_{0-4}SC(O)R^\circ$; $-(CH_2)_{0-4}C(O)NR^\circ)_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)$O-N(R^\circ)_2$; or $-(C_{1-4}$ straight or branched)alkylene)$C(O)O-N(R^\circ_2$, wherein each $R^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aromatic ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aromatic mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$, $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR-$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-(CH_2)_{0-1}Ph$, or a 5-6-membered saturated, partially unsaturated, or aromatic ring having 0-4 heteroatoms independently selected from nitrogen, oxygen, or sulfur. Such divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aromatic ring having 0-4 heteroatoms independently selected from nitrogen, oxygen, or sulfur. Divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aromatic ring having 0-4 heteroatoms independently selected from nitrogen, oxygen, or sulfur. A tetravalent substituent that is bound to vicinal substitutable methylene carbons of an "optionally substituted" group is the dicobalt hexacarbonyl cluster represented by

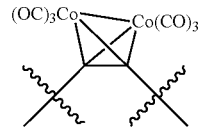

when depicted with the methylenes which bear it.

Suitable substituents on the aliphatic group of $R^*$ include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aromatic ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aromatic ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aromatic mono- or bicyclic ring having 0-4 heteroatoms independently selected from nitrogen, oxygen, or sulfur.

Suitable substituents on the aliphatic group of $R^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, or sulfur.

Suitable substituents also include protecting groups, such as those described in detail in Wuts, P. G. M. *Protecting Groups in Organic Synthesis*, 5$^{th}$ Ed., New York, John Wiley & Sons, 2014, the entirety of which is incorporated herein by reference.

Examples of suitably protected hydroxyl groups include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of carbonates include 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl carbonate. Examples of silyl ethers include trimethylsilyl, triethylsilyl, t-butyldimethylsilyl, t-butyldiphenylsilyl, triisopropylsilyl ether, and other trialkylsilyl ethers. Examples of alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Examples of mono-protected aminos include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Di-protected aminos include aminos that are substituted with two substituents independently selected from those described above as mono-protected aminos, and further include cyclic imides, such as phthalimide, maleimide, succinimide, and the like. Di-protected aminos also include pyrroles and the like, 2,2,5,5-tetramethyl-[1,2,5]azadisilolidine and the like, and azide.

Protected aldehydes include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl esters, wherein each group is optionally substituted. Additional protected carboxylic acids include oxazolines and ortho esters.

Protected thiols include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester.

In a particular embodiment, suitable substituents are selected from —(CH$_2$)$_{0-4}$Ph (e.g., —CH$_2$Ph), which may be optionally substituted with halogen, —(CH$_2$)$_{0-2}$R$^\bullet$, -(haloR$^\Theta$), —(CH$_2$)$_{0-2}$OH, —(CH$_2$)$_{0-2}$OR$^\bullet$, —O(haloR$^\bullet$), —CN, —N$_3$, —(CH$_2$)$_{0-2}$SR$^\bullet$, —(CH$_2$)$_{0-2}$SH or —NO$_2$, wherein each R$^\bullet$ is unsubstituted or where preceded by "halo" is substituted only with one or more halogens, and is independently selected from $C_{1-4}$ aliphatic (e.g., $C_1$ aliphatic). In another embodiment, suitable substituents are selected from a protecting group or —(CH$_2$)$_{0-4}$Ph (e.g., —CH$_2$Ph), which may be optionally substituted with halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —O(haloR$^\bullet$), —CN, —N$_3$, —(CH$_2$)$_{0-2}$SR$^\bullet$, —(CH$_2$)$_{0-2}$SH or —NO$_2$, wherein each R$^\bullet$ is unsubstituted or where preceded by "halo" is substituted only with one or more halogens, and is independently selected from $C_{1-4}$ aliphatic (e.g., $C_1$ aliphatic).

In some embodiments, suitable substituents are selected from halogen, hydroxy, cyano, nitro, oxo, phenyl, azido, or alkynyl, wherein phenyl is substituted with 0-5 (e.g., 0-3) substituents independently selected from halogen, —CH$_3$, —CF$_2$H, —CF$_3$, —OCH$_3$, —OCF$_3$ or —OH. In some embodiments, an optionally substituted group or compound, such as an optionally substituted aliphatic, is substituted with 0-5 (e.g., 0-3) substituents independently selected from halogen, hydroxy, cyano, nitro, oxo, phenyl, azido, or alkynyl, wherein phenyl is substituted with 0-5 (e.g., 0-3) substituents independently selected from halogen, —CH$_3$, —CF$_2$H, —CF$_3$, —OCH$_3$, —OCF$_3$ or —OH.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of ixabepilone include salts derived from suitable inorganic and organic acids that are compatible with the treatment of subjects. Pharmaceutically acceptable salts of a copolymer described herein include salts derived from suitable inorganic and organic acids and inorganic and organic bases that are compatible with the treatment of subjects. In some embodiments, ixabepilone and/or a copolymer described herein is provided as a pharmaceutically acceptable salt.

Examples of pharmaceutically acceptable, nontoxic acid addition salts are salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art such as ion-exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited to, hydrochloric, hydrobromic, sulfuric and phosphoric acid and acid metal salts, such as sodium monohydrogen orthophosphate and potassium hydrogen sulfate. Illustrative organic acids which form suitable salts include mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids, such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts are most suitably formed from pharmaceutically acceptable acids, and include, for example, those formed with inorganic acids, e.g., hydrochloric, sulfuric or phosphoric acids, and organic acids, e.g., succinic, maleic, acetic or fumaric acid.

Illustrative inorganic bases which form suitable salts include, but are not limited to, lithium, sodium, potassium, calcium, magnesium or barium hydroxides. Illustrative organic bases which form suitable salts include aliphatic, alicyclic or aromatic organic amines, such as methylamine, trimethyl amine and picoline, or ammonia. The selection criteria for the appropriate salt will be known to one skilled in the art.

Salts derived from appropriate bases include alkali metal, alkaline earth metal, ammonium and $N^+((C_1-C_4) \text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Unless otherwise stated, the compounds described herein (e.g., ixabepilone, or a pharmaceutically acceptable salt thereof; a copolymer described herein) are also meant to include compounds that differ only in the presence of one or more isotopically enriched atoms. Examples of isotopes that can be incorporated into compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$ and $^{125}I$, respectively. Such isotopically labelled compounds are useful, for example, in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Substitution with heavier isotopes, particularly deuterium (i.e., $^2H$ or D) may afford certain therapeutic advantages resulting from greater metabolic stability, for example, increased in vivo half-life or reduced dosage requirements or an improvement in therapeutic index.

Isotopically labeled compounds of the present disclosure can generally be prepared by conventional techniques known to those skilled in the art by substituting an appropriate or readily available isotopically labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging.

Copolymers

Provided herein are multiblock poly(amino acid) copolymers comprising a poly(sarcosine) block and a block (e.g., a hydrophobic block) comprising a mixture (e.g., an atactic mixture) of D- and L-amino acids. When the block comprising a mixture of D- and L-amino acids is hydrophobic, the copolymers can spontaneously self-assemble into micelles in aqueous solution when the concentration of the copolymer is above the critical micelle concentration, with the hydrophilic poly(sarcosine) block forming the corona of the micelle and the hydrophobic block comprising a mixture of D- and L-amino acids forming the core of the micelle. Accordingly, in some embodiments of a copolymer described herein, the copolymer is capable of forming a micelle, e.g., in aqueous solution, when the concentration of the copolymer is above the critical micelle concentration.

In a first embodiment, the copolymer is represented by formula I:

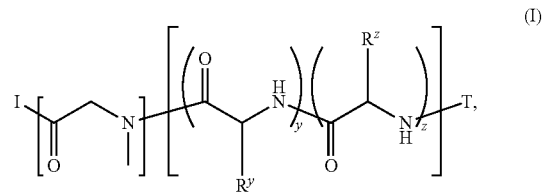

wherein:
I is an initiating group;
T is a terminal group;
$R^y$ and $R^z$ are each independently an amino acid side chain, wherein $R^y$, taken together with the amino acid backbone to which it is attached, forms a D-amino acid and $R^z$, taken together with the amino acid backbone to which it is attached, forms an L-amino acid;
x is an integer from 125 to 350 (e.g., 150 to 300, 150 to 250, 150 to 200);

y is an integer from 5 to 35 (e.g., 10 to 35, 15 to 30, 20 to 35, 20 to 25, 25 to 35, 30 to 35); and z is an integer from 5 to 35 (e.g., 10 to 35, 15 to 30, 20 to 35, 20 to 25, 25 to 35, 30 to 35).

In a first aspect of the first embodiment, I is amino, hydroxyl, alkoxy, thio or thioalkoxy (e.g., amino, such as neopentylamino). The remaining variables are as described in the first embodiment.

In a second aspect of the first embodiment, T is a living polymer chain-end (e.g., hydrogen). Values for the remaining variables are as described in the first embodiment, or first aspect thereof.

In a third aspect of the first embodiment, T is a capping group (e.g., an acyl group, such as acetyl; a detectable label). Values for the remaining variables are as described in the first embodiment, or first or second aspect thereof.

In a fourth aspect of the first embodiment, $R^y$ and $R^z$, taken together with the amino acid backbones to which they are attached, form a hydrophobic block. Values for the remaining variables are as described in the first embodiment, or first through third aspects thereof.

In a fifth aspect of the first embodiment, $R^y$, taken together with the amino acid backbone to which it is attached, forms an amino acid selected from glycine, alanine, isoleucine, leucine, methionine, phenylalanine, tryptophan, tyrosine, valine, proline, asparagine, glutamine or γ-benzylglutamate (e.g., leucine). Values for the remaining variables are as described in the first embodiment, or first through fourth aspects thereof.

In a sixth aspect of the first embodiment, $R^z$, taken together with the amino acid backbone to which it is attached, forms an amino acid selected from glycine, alanine, isoleucine, leucine, methionine, phenylalanine, tryptophan, tyrosine, valine, proline, asparagine, glutamine or γ-benzylglutamate (e.g., tyrosine). Values for the remaining variables are as described in the first embodiment, or first through fifth aspects thereof.

In a seventh aspect of the first embodiment, x is an integer from 140 to 210 (e.g., 175). Values for the remaining variables are as described in the first embodiment, or first through sixth aspects thereof.

In an eighth aspect of the first embodiment, y is 30. Values for the remaining variable are as described in the first embodiment, or first through seventh aspects thereof.

In a ninth aspect of the first embodiment, y is 35. Values for the remaining variables are as described in the first embodiment, or first through eighth aspects thereof.

In a tenth aspect of the first embodiment, z is 25. Values for the remaining variables are as described in the first embodiment, or first through ninth aspects thereof.

In an eleventh aspect of the first embodiment, z is 20. Values for the remaining variables are as described in the first embodiment, or first through tenth aspects thereof.

In a twelfth aspect of the first embodiment, y is 30 and z is 20. Values for the remaining variables are as described in the first embodiment, or first through eleventh aspects thereof.

In a thirteenth aspect of the first embodiment, the sum of y and z is 75 or less (e.g., 60 or less, such as 40 to 60, 40 to 55, 40 to 50, 50, 60). Values for the remaining variables are as described in the first embodiment, or first through twelfth aspects thereof.

In a fourteenth aspect of the first embodiment, y is from 10% to 90% (e.g., about 60%) of the sum of y and z. Values for the remaining variables are as described in the first embodiment, or first through thirteenth aspects thereof.

In a fifteenth aspect of the first embodiment, z is from 10% to 90% (e.g., about 40%) of the sum of y and z. Values for the remaining variables are as described in the first embodiment, or first through fourteenth aspects thereof.

In a sixteenth aspect of the first embodiment, the copolymer is capable of forming a micelle (e.g., in aqueous solution, when the concentration of the copolymer is above the critical micelle concentration). Values for the variables are as described in the first embodiment, or first through fifteenth aspects thereof.

In a seventeenth aspect of the first embodiment, $R^y$, taken together with the amino acid backbone to which it is attached, forms a hydrophobic amino acid. Values for the remaining variables are as described in the first embodiment, or first through sixteenth aspects thereof.

In an eighteenth aspect of the first embodiment, $R^z$, taken together with the amino acid backbone to which it is attached, forms a hydrogen bonding amino acid (e.g., a hydrophilic amino acid). Values for the remaining variables are as described in the first embodiment, or first through seventeenth aspects thereof.

In a second embodiment, the copolymer is represented by formula II:

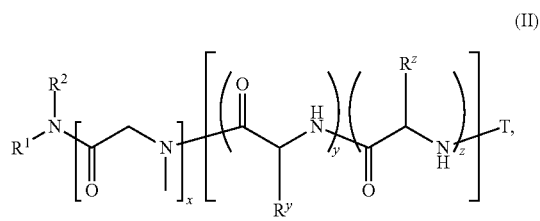

(II)

wherein $R^1$ and $R^2$ are each independently hydrogen or optionally substituted $(C_1-C_{10})$aliphatic and the remaining variables (e.g., T, $R^y$, $R^z$, x, y, z) are as described in the first embodiment, or any aspect thereof.

In a first aspect of the second embodiment, $R^1$ is hydrogen and $R^2$ is optionally substituted $(C_1-C_{10})$aliphatic (e.g., optionally substituted $(C_1-C_{10})$alkyl, such as neopentyl). Values for the remaining variables are as described in the first embodiment, or any aspect thereof, or second embodiment.

In a third embodiment, the copolymer is represented by formula III:

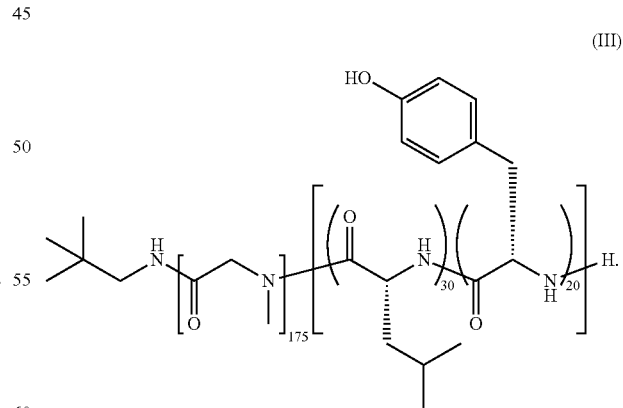

(III)

The copolymer represented by formula III is also referred to herein as "TFS-2," "poly(sarcosine)$_{175}$-block-poly(d-leucine$_{30}$-co-l-tyrosine$_{20}$)," "PSar$_{175}$-P(dLeu$_{30}$/lTyr$_{20}$)," and "poly[Sar$_{175}$]-block-poly-[D-Leu$_{30}$-co-L-Tyr$_{20}$]."

In a fourth embodiment, the copolymer is represented by formula IV:

(IV)

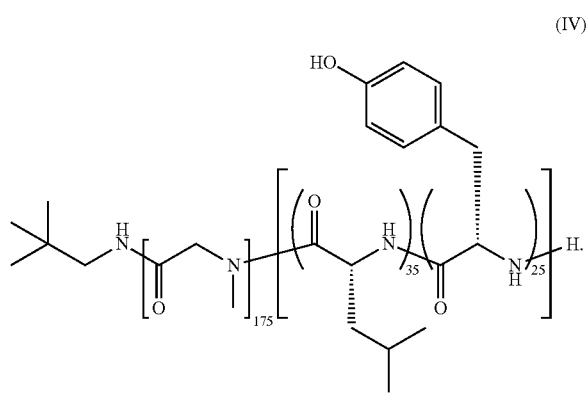

The copolymer represented by formula IV is also referred to herein as "TFS-1", "poly(sarcosine)$_{175}$-block-poly(d-leucine$_{35}$-co-l-tyrosine$_{25}$)," "PSar$_{175}$-P(dLeu$_{35}$/lTyr$_{25}$)" and "poly[Sar$_{175}$]-block-poly-[D-Leu$_{35}$-co-L-Tyr$_{25}$]."

In a fifth embodiment, the copolymer is represented by formula (V):

(V)

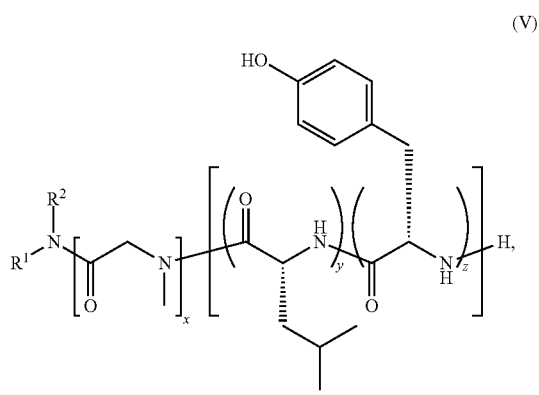

wherein the variables (e.g., $R^1$, $R^2$, x, y, z) are as described in the first through fourth embodiments, or any aspect thereof.

Compositions, Unit Dose Forms and Kits

Provided herein are compositions (e.g., pharmaceutical compositions) of ixabepilone, or a pharmaceutically acceptable salt thereof. Ixabepilone is a microtubule inhibitor belonging to the epothilone class of antineoplastic agents. The chemical name for ixabepilone is (1S,3S,7S,10R,11S,12S,16R)-7,11dihydroxy-8,8,10,12,16-pentamethyl-3-[(1E)-1-methyl-2-(2-methyl-4-thiazolyl)ethenyl]17-oxa-4-azabicyclo[14.1.0] heptadecane-5,9-dione. Ixabepilone has the following structural formula:

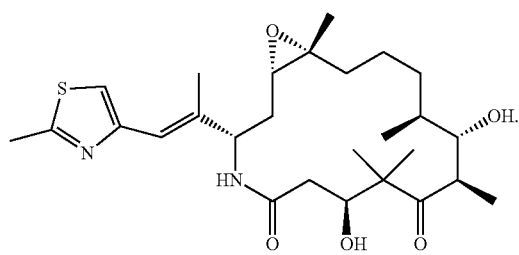 [SMILES: C/C(=C\c1csc(C)n1)[C@@H]1C[C@@H]2O[C@]2(C)CCC[C@H](C)[C@H](O)[C@@H](C)C(=O)C(C)(C)[C@@H](O)CC(=O)N1]

In one embodiment, the composition comprises ixabepilone, or a pharmaceutically acceptable salt thereof (e.g., ixabepilone), and a copolymer described herein (e.g., TFS-2).

In some embodiments, the composition further comprises a cryoprotectant. "Cryoprotectant," as used herein, refers to a chemical that prevents or substantially prevents freezing damage. Examples of cryoprotectants include glycine, trehalose, sucrose, glycerol, dimethylsulfoxide, lactose, mannitol and polyethylene glycol. Further examples of cryoprotectants include sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose. Examples of preferred cryoprotectants include glycine and trehalose (e.g., glycine).

In some embodiments, the composition has a feed ratio from about 1% to about 50%. In some embodiments, the feed ratio is from about 10% to about 50%. In some embodiments, the feed ratio is about 20%.

"Feed ratio," as used herein, refers to the ratio of drug (e.g., ixabepilone, or a pharmaceutically acceptable salt thereof) to copolymer (e.g., TFS-1, TFS-2) in a composition described herein. Feed ratio is expressed as a weight percentage (% w/w). For example, 100 mg of a drug combined with 500 mg of a copolymer would be expressed as a feed ratio of 20% (100 mg/500 mg×100=20%). Feed ratio is independent of other components present in the drug product. Thus, a 10% feed ratio may result in a drug product containing 5% drug by weight when other components of the drug product are taken into account. Representative feed ratios include from about 1% to about 50%, from about 5% to about 50%, from about 10% to about 50%, from about 10% to about 40%, from about 15% to about 25%, about 4%, about 5%, about 10%, about 15%, about 20%, about 25%, about 30%, about 35% or about 40%.

It will be understood that when $R^y$ and $R^z$, taken together with the amino acid backbones to which they are attached, form a hydrophobic block, the copolymers described herein comprise a hydrophilic block formed by the poly(sarcosine) block, and a hydrophobic block formed by the poly(amino acid) block. Such copolymers often spontaneously self-assemble into micelles in aqueous solutions when the concentration of the copolymer is above the critical micelle concentration. It is believed that a multiblock copolymer comprising poly(sarcosine) and a hydrophobic poly(amino acid) block will form a micelle with a poly(sarcosine) corona and a hydrophobic poly(amino acid) core. Such micelles are useful for encapsulating hydrophobic molecules, such as ixabepilone, thereby forming mixed micelles. Without wishing to be bound by any particular theory, it is believed that if a hydrophobic molecule, such as ixabepilone, is present during the self-assembly of the micelle, the hydrophobic molecule will be sequestered in the hydrophobic core of the micelle.

"Mixed micelle," as used herein, refers to a micelle comprising at least two different molecular species. In some embodiments, the composition is in the form of mixed micelles, e.g., comprising ixabepilone, or a pharmaceutically acceptable salt thereof, and a copolymer (e.g., a copolymer capable of forming a micelle). When a composition described herein is in the form of mixed micelles comprising ixabepilone, or a pharmaceutically acceptable salt thereof, and a multiblock copolymer comprising poly(sarcosine) and a hydrophobic poly(amino acid) block, it is believed that the poly(sarcosine) block will form the corona of the mixed micelle, and the hydrophobic poly(amino acid)

block and ixabepilone, or a pharmaceutically acceptable salt thereof, will form the core of the mixed micelle.

In some embodiments, the composition comprises from about 1% to about 25%, from about 1% to about 5%, from about 5% to about 15%, from about 5% to about 10%, from about 10% to about 15%, from about 15% to about 20%, from about 20% to about 25%, e.g., about 5%, about 6%, about 7%, about 8%, about 9%, about 10%, about 11%, about 12%, about 13%, about 14%, about 15%, about 20% or about 25%, ixabepilone, or a pharmaceutically acceptable salt thereof, by weight. In some embodiments, the composition comprises about 10% ixabepilone, or a pharmaceutically acceptable salt thereof, by weight.

In some embodiments, the composition comprises from about 40% to about 50%, e.g., about 40%, about 41%, about 42%, about 43%, about 44%, about 45%, about 46%, about 47%, about 48%, about 49% about 50%, copolymer by weight. In some embodiments, the composition comprises about 45% copolymer by weight.

In some embodiments, the composition comprises from about 40% to about 50%, e.g., about 40%, about 41%, about 42%, about 43%, about 44%, about 45%, about 46%, about 47%, about 48%, about 49% about 50%, cryoprotectant by weight. In some embodiments, the composition comprises about 45% cryoprotectant by weight.

One embodiment is a composition comprising about 10% ixabepilone by weight, about 45% TFS-2 by weight, and about 45% trehalose or glycine (e.g., glycine) by weight.

One embodiment is a unit dose form of a composition comprising about 20 mg ixabepilone, about 180 mg TFS-2; and about 180 mg glycine.

In some embodiments, the compositions described herein are in solid form. When a composition described herein is in solid form, it can be reconstituted in a diluent, e.g., for administration (e.g., intravenous administration) to a subject. The reconstituted composition or unit dose form can be administered to a subject directly or further diluted, e.g., into intravenous fluid for administration to a subject. Thus, in some embodiments, the composition and/or unit dose form further comprises a diluent (e.g., 0.9% sodium chloride for injection). In yet further embodiments, the composition and/or unit dose form comprises about 10 mL diluent (e.g., 10 mL 0.9% sodium chloride for injection).

"Diluent," as used herein, refers to a liquid used to reconstitute a dry substance for administration (e.g., intravenous administration). Diluents are inactive ingredients of drug products. Examples of diluents include water, 0.9% sodium chloride for injection (normal saline), 5% dextrose for injection (D5W), Ringer's injection, and lactated Ringer's injection.

Compositions described herein may be suitable for administration and/or administered orally, parenterally (including subcutaneously, intramuscularly, intravenously and intradermally), by inhalation spray, topically, rectally, nasally, buccally, vaginally or via an implanted reservoir. The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal, intralesional and intracranial injection or infusion techniques. Preferably, the compositions are suitable for intravenous administration.

Compositions provided herein can be orally administered in any orally acceptable dosage form including, but not limited to, capsules, tablets, aqueous suspensions, dispersions and solutions. Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, gelatin or glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

An agent can also be in micro-encapsulated form with one or more excipients, as noted above. In such solid dosage forms, the agent can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In one embodiment, the composition is an immediate-release composition. Alternatively, the composition is an extended (or "delayed" or "sustained") release composition. This delayed-release composition comprises an agent in combination with a delayed-release component. Such a composition allows targeted release of a provided agent into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered in the form of suppositories for rectal administration. These can be prepared by mixing an agent with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration of an agent include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active component suspended or dissolved in one or more pharmaceutically acceptable carriers. Alternatively, the composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

It should also be understood that a specific dosage and treatment regimen for any particular patient will depend upon a variety of factors, including the activity of the specific agent employed, the age, body weight, general health, sex, diet, time of administration, rate of excretion, drug combination, the judgment of the treating physician and the severity of the particular disease being treated. The amount of an agent in the composition will also depend upon the particular agent in the composition.

Other pharmaceutically acceptable carriers, adjuvants and vehicles that can be used in the compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

Ixabepilone can be administered as part of a combination therapy with one or more additional therapeutic agents to treat a disease or condition described herein (e.g., cancer). Compositions for use in combination therapies can either be formulated together as a combination, or provided for separate administration (e.g., associated in a kit). Accordingly, in some embodiments, a composition described herein further comprises one or more additional therapeutic agents (e.g., capecitabine). Some embodiments provide a kit comprising a composition described herein and one or more additional therapeutic agents (e.g., capecitabine).

Also provided herein is a kit comprising a composition described herein and a diluent, such as a diluent described herein (e.g., about 10 mL diluent). In certain aspects, the kit further comprises one or more additional therapeutic agents (e.g., capecitabine).

In some embodiments, a kit described herein further comprises directions for reconstituting and/or administering the composition and, optionally, the one or more additional therapeutic agents.

Methods of Treatment

Also provided is a method for treating cancer in a subject in need thereof, comprising administering to the subject an effective amount of a composition and/or a unit dose form described herein.

"Treat," "treating" and "treatment," as used herein, refer to the administration of a medication or medical care to a subject, such as a human, having a disease or condition described herein such that: (i) the disease or condition is prevented from occurring in a subject, in particular, when such subject is predisposed to the condition but has not yet been diagnosed as having it; (ii) the disease or condition is inhibited, e.g., delayed or arrested in its development; (iii) the disease or condition is relieved, e.g., regresses; and/or (iv) one or more symptoms resulting from the disease or condition is relieved (e.g., pain, weight loss, cough, fatigue, weakness, etc.).

As used herein, the term "subject" refers to an animal. Typically, the animal is a mammal, for example, primate (e.g., human), cow, sheep, goat, horse, dog, cat, rabbit, rat, mouse, fish, bird and the like. In preferred embodiments, the subject is a human.

A "subject in need thereof" is a subject who has, or is at risk for developing, a disease or condition described herein (e.g., cancer).

"Effective amount," as used herein, refers to an amount of a therapeutic agent, such as ixabepilone, that, when administered to a subject, such as a human, is sufficient to effect treatment. The amount of a therapeutic agent that constitutes an "effective amount" will vary depending on the therapeutic agent, the condition being treated and its severity, the manner of administration, the duration of treatment, or the subject to be treated (e.g., age, weight, fitness of the subject), but can be determined routinely by one of ordinary skill in the art based on his own knowledge and this disclosure. In embodiments, an "effective amount" effects treatment as measured by a statistically significant change in one or more indications, symptoms, signs, diagnostic tests, vital signs, and the like. In other embodiments, an "effective amount" manages or prevents a condition as measured by a lack of a statistically significant change in one or more indications, symptoms, signs, diagnostic tests, vital signs, and the like.

The compositions and/or dose forms described herein are useful in the treatment of a variety of cancers, including (i) carcinoma, including that of the bladder, breast, colon, kidney, liver, lung, ovary, pancreas, stomach, cervix, thyroid and skin, including squamous cell carcinoma; (ii) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma; (iii) hematopoietic tumors of myeloid lineage, including acute and chronic myelogenous leukemias and promyelocytic leukemia; (iv) tumors of the central and peripheral nervous system, including astrocytoma, neuroblastoma, glioma and schwannoma; (v) tumors of mesenchymal origin, including fibrosarcoma, rhabdomyosarcoma and osteosarcoma; and (vi) other tumors including melanoma, xenoderma, pigmentosum, keratoactanthoma, seminoma, thyroid follicular cancer and teratocarcinoma.

Further examples of cancers treatable according to the methods described herein include, but are not limited to, Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sézary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CIVIL); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sézary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein.

Other diseases and conditions that can be treated using the compositions and/or dose forms described herein are described in U.S. Pat. Nos. RE 41,911; RE 41,393; 6,670,384; 7,022,330; and 7,312,237, the relevant contents of which are incorporated herein by reference in their entirety.

In some embodiments, the cancer is breast cancer, bladder cancer, pancreatic cancer, prostate cancer, non-small cell lung cancer or colorectal cancer (e.g., breast cancer).

In some embodiments, the cancer is metastatic or locally advanced. In some embodiments, the cancer is metastatic or locally advanced breast cancer.

"Metatstatic," used herein to describe cancer, refers to cancer that has spread from the part of the body where it started to other parts of the body.

"Locally advanced," used herein to describe cancer, refers to cancer that has grown outside the organ it started in but has not yet spread to distant parts of the body.

In some embodiments, the subject failed a prior therapy comprising an anthracycline, a taxane, capecitabine or any combination thereof. In some embodiments, the subject failed a prior therapy comprising an anthracycline, a taxane and capecitabine. In some embodiments, the subject failed a prior therapy comprising an anthracycline and a taxane.

A subject is said to have "failed" a therapy herein if the subject relapses from the therapy, or is resistant or refractory to the therapy (e.g., progresses following or while on the therapy). For example, treatment of a subject having breast cancer that has not metastasized or advanced locally may not prevent the breast cancer from metastasizing or advancing locally. If the treatment does not prevent the breast cancer from metastasizing or advancing locally, and the breast cancer metastasizes and/or advances locally, the subject is said to have failed the treatment because the subject's cancer progressed following or while on the treatment. In another example, a subject previously diagnosed with metastatic or locally advanced breast cancer may be treated with a therapy for such cancer, but fail to respond to the therapy. This subject, too, is said to have failed the therapy because the subject is resistant or refractory to the therapy. Similarly, a subject that experiences remission following a therapy, but subsequently relapses, is considered to have failed the prior therapy.

"Prior therapy," as used herein, refers to any therapy given before the referenced therapy for a disease or condition. When a prior therapy includes drug(s), the referenced or subsequent therapy comprises one or more drugs that are different from the drug(s) of the prior therapy. In some embodiments, the subsequent therapy is a second-line therapy (i.e., the second therapy given for a disease or condition). In some embodiments, the subsequent therapy is a third-line therapy (i.e., the third therapy given for a disease or condition). In some embodiments, the subsequent therapy is a fourth-line therapy (i.e., the fourth therapy given for a disease or condition).

The compositions and/or unit dose forms described herein can be administered orally, parenterally (including subcutaneously, intramuscularly, intravenously and intradermally), by inhalation spray, topically, rectally, nasally, buccally, vaginally or via an implanted reservoir. Preferably, the compositions and/or unit dose forms are administered intravenously.

The compositions and/or unit dose forms described herein can also be administered in combination with one or more additional therapies (e.g., radiation therapy, chemotherapy, immunotherapy). Accordingly, in some embodiments, the methods of treatment further comprises administering to the subject one or more additional therapies (e.g., an effective amount of one or more additional therapies). In some embodiments, a method of treatment described herein further comprises administering to the subject one or more additional therapeutic agents (e.g., capecitabine).

When administered in combination with an additional therapy, the composition and/or unit dose form described herein can be administered before, after or concurrently with the additional therapy (e.g., an additional therapeutic agent(s)). When two or more therapeutic agents are co-administered simultaneously (e.g., concurrently), the composition and/or unit dose form described herein and additional therapeutic agent(s) can be in separate formulations or the same formulation. Alternatively, the composition and/or unit dose form described herein and the additional therapy can be administered sequentially (e.g., as separate compositions) within an appropriate time frame as determined by a skilled clinician (e.g., a time sufficient to allow an overlap of the pharmaceutical effects of the composition and/or unit dose form described herein and the additional therapy).

One embodiment is a method for treating metastatic or locally advanced breast cancer in a human who has failed a prior treatment comprising an anthracycline and a taxane, comprising administering to the human an effective amount of a composition or a unit dose form described herein; and capecitabine.

One embodiment is a method for treating metastatic or locally advanced breast cancer in a human who has failed a prior treatment comprising an anthracycline, a taxane and capecitabine, comprising administering to the human an effective amount of a composition or a unit dose form described herein.

Methods of Manufacture

Also provided herein is a method of preparing a composition and/or a unit dose form described herein. The method comprises dissolving ixabepilone, or a pharmaceutically acceptable salt thereof, a copolymer described herein and, optionally, a cryoprotectant in aqueous tert-butanol, thereby forming a mixed solution; and lyophilizing the mixed solution, thereby preparing the composition or unit dose form.

In some embodiments, the method of preparing a composition and/or a unit dose form described herein comprises dissolving ixabepilone, or a pharmaceutically acceptable salt thereof, in a first portion of aqueous tert-butanol, thereby forming an ixabepilone solution; dissolving a copolymer described herein and, optionally, a cryoprotectant in a second portion of aqueous tert-butanol, thereby forming a copolymer solution; mixing the ixabepilone solution and the copolymer solution, thereby forming a mixed solution; filtering the mixed solution, thereby forming a filtered solution; and lyophilizing the filtered solution.

In some embodiments, the method further comprises maintaining the mixed solution and/or the ixabepilone solution at a temperature of less than 23° C. (e.g., about 15° C.).

In some embodiments, the method of preparing a composition and/or a unit dose form described herein comprises dissolving ixabepilone in a first aqueous solution of tert-butanol (e.g., 5% solution of water in tert-butanol), thereby forming an ixabepilone solution, and cooling the ixabepilone solution to about 15° C. A copolymer (e.g., TFS-2) and cryoprotectant (e.g., glycine) are dissolved in a second aqueous solution of tert-butanol (e.g., 30% solution of tert-butanol in water), thereby forming a copolymer solution. The ixabepilone solution and copolymer solution are mixed, while maintaining a temperature of about 15° C., thereby forming a mixed solution. The mixed solution is aseptically filtered (e.g., through a 0.22-μm PVDF filter), thereby forming a filtered solution, and the filtered solution is lyophilized.

In some embodiments, the method of preparing a composition and/or a unit dose form described herein further comprises diluting the composition or unit dose form (e.g., the lyophilized composition or unit dose form) in a diluent, such as any of the diluents described herein in any amount described herein.

EXEMPLIFICATION

Example 1. Preparation of Representative Copolymers and Identification of TFRP-1

Novel diblock copolymers were developed and synthesized. Of approximately 10 copolymers screened, five copolymers were selected for formulation screening with ixabepilone. The structures of the five selected polymers are shown below.

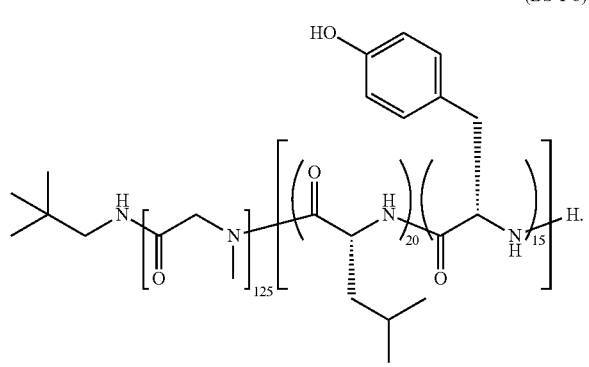
(BS-I-8)

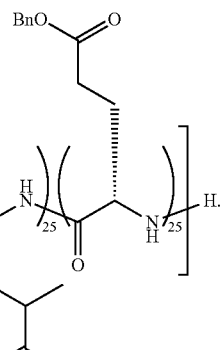
(BS-I-9)

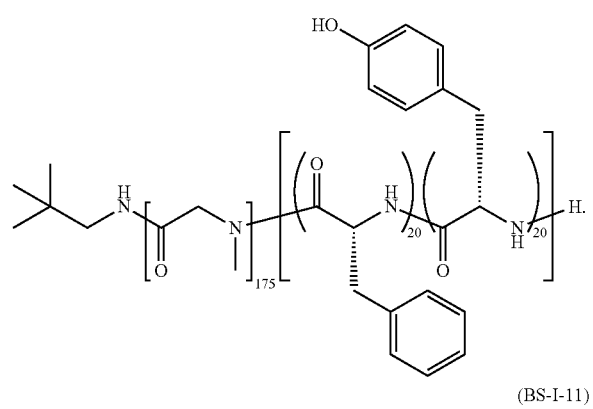
(BS-I-10)

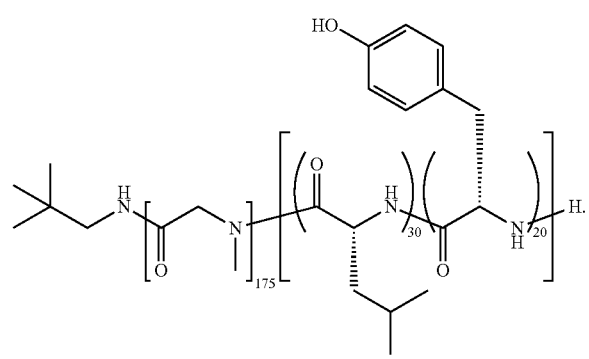
(BS-I-11)

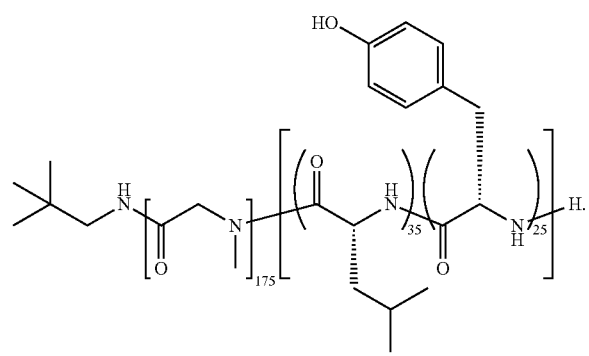
(BS-I-12)

Infrared (IR) Spectroscopy. All samples were analyzed using a PerkinElmer Spectrum 100 FT-IR Spectrometer equipped with Universal ATR Sampling Accessory (Diamond/ZnSe). When using IR to monitor a reaction, an aliquot of approximately 100 μL was taken and measured directly. Solid samples were measured without further manipulation.

Nuclear Magnetic Resonance (NMR) Spectroscopy. All samples were analyzed in a 400 MHz spectrometer with the following parameters: 45° pulse, 2 second acquisition time, 5 second recycle delay, with 16-32 transients.

Gel Permeation Chromatography (GPC) Analysis. Samples were analyzed using a Shimadzu LC-20AD pump connected in series to: 2×PSS GRAM analytical 100 Å, 8×300 mm, 10 μm columns; 1×PSS GRAM analytical 1000 Å, 8×300 mm, 10 μm column; a Wyatt TREOS II Light Scattering Detector, and a Wyatt Optilab T-rEX refractive index detector. A mobile phase of DMF supplemented with LiBr (50 mM) at a flow rate of 1.0 mL was used to elute the analytes. The temperature of the columns was maintained at 45° C. Typically, run times of 45 minutes were employed. GPC number-average molecular weight (Mn) and peak molecular weight (Mp) were calibrated using polystyrene molecular weight standards.

HPLC Analysis. Assay and identity of ixabepilone was determined by high pressure liquid chromatography (HPLC) with ultraviolet (UV) detection at 240 nm. The column utilized was a Phenomenex Gemini® 5 μm C18 (110 Å, 250×4.6 mm) at ambient temperature. Mobile phase A consisted of 90% 5 mM Tris buffer (pH 8.5):10% acetonitrile and Mobile Phase B consisted of 10% 5 mM Tris buffer (pH 8.5):90% acetonitrile. Ixabepilone samples were prepared by dissolving the material in a 1:2 mixture of Mobile Phase A:Mobile Phase B. Ixabepilone standards were prepared by dissolving the material in acetonitrile. Separation was achieved with a flow rate of 1.8 mL/min using the following gradient:

| Time (minutes) | % A | % B | Gradient Profile |
|---|---|---|---|
| 0-0.25 | 70.0 | 30.0 | Isocratic hold |
| 2.5-10.0 | 70.0-60.6 | 30.0-39.4 | Linear |
| 10.0-20.0 | 60.6-35.0 | 39.4-65.0 | Linear |
| 20.0-22.0 | 35.0-12.5 | 65.0-87.5 | Linear |
| 22.0-25.0 | 12.5 | 87.5 | Isocratic hold |
| 25.0-25.1 | 12.5-70.0 | 87.5-30.0 | Linear |
| 25.1-31.0 | 70.0 | 30.0 | Isocratic hold |

Weight Loading Analysis. Weight loading was determined by comparing a standard curve of ixabepilone to a known concentration of drug product by HPLC analysis. Standards were prepared by dissolving ixabepilone in acetonitrile at concentrations of 10, 25, 50, and 100 μg/mL. Ixabepilone drug product samples were prepared by dissolving the material in a 1:2 mixture of Mobile Phase A:Mobile Phase B at a concentration of 1 mg/mL. The amount of ixabepilone in the drug product was then converted to weight percentage of the total based on the known quantity of drug product (i.e., 1 mg/mL).

Preparation of $Sar_{175}$-b-p-[$D$-$Leu_{35}$-co-$L$-$Tyr_{25}$] (TFS-1, BS-I-12). A jacketed, round-bottomed flask equipped to a circulating isopropanol/water bath was charged with N,N-dimethylformamide (DMF; 100 mL). The bath temperature was set to 20° C., and the DMF was stirred for approximately 15 minutes to equilibrate before the addition of a solution of neopentylamine (3.31 mL of 300 mM in DMF, 86.6 mg, 1 equiv.) followed by sarcosine N-carboxyanhydride (20.0 g, 173.8 mmol, 175 equiv.). The sides of the funnel and reaction vessel were rinsed down with additional DMF (approximately 5 mL). The reaction vessel was wrapped in aluminum foil to prevent light. As the reaction proceeded, the color of the reaction solution changed from clear and colorless to clear and bright orange. IR was used to monitor the reaction progression via disappearance of the carbonyl stretches at approximately 1850 and 1778 cm$^{-1}$. After 8 hours, the reaction was >95% complete, but was left overnight (additional 12 hours). The bath temperature was set to 25° C., and then the reaction was charged with D-leucine N-carboxyanhydride (5.46 g, 34.77 mmol, 35 equiv.) and L-tyrosine N-carboxyanhydride (5.15 g, 24.84 mmol, 25 equiv.). The consumption of the two N-carboxyanhydrides (NCAs) was again monitored via the disappearance of the IR carbonyl stretches at approximately 1851 and 1785 cm$^{-1}$, and the reaction was complete after approximately 24 hours. The reaction mixture was transferred to a beaker using a small amount of DMF (approximately 5-10 mL). While stirring vigorously with an overhead stirrer, ethyl acetate (480 mL, approximately 4 volumes) was added slowly over 1-2 minutes. The precipitation was quick, and noticeable solids started to form after the addition of <1 volume of EtOAc. The precipitation was stirred for 5-10 minutes to mechanically break apart any large solids and to leach out DMF, which can become trapped in the solids. The stirring was stopped, and the material was allowed to settle before being collected via vacuum filtration in a medium porosity fritted glass funnel. The semi-dry material was slurried briefly on the frit with an additional 2 volumes (240 mL) of EtOAc. The product was dried in a vacuum oven at 90-100° C. for 2 days to yield 19.8 g (97%) of the title compound as a fine, off-white dense powder. $^1$H NMR (DMSO-$d_6$) δ 9.2-9.0 (30H), 8.6-7.8 (48H), 7.2-6.5 (125H), 4.7-3.7 (845H), 3.0-2.6 (1440H), 1.9-1.2 (104H), 1.0-0.5 (289H); GPC (DMF, 50 mM LiBr) Mn=17.6 kDa, Mp=18.7 kDa, PDI=1.08.

Preparation of $Sar_{175}$-b-p-[$D$-$Leu_{30}$-co-$L$-$Tyr_{20}$] (TFS-2, BS-I-11). A jacketed, round-bottomed flask equipped to a circulating isopropanol/water bath was cooled to 20° C. prior to the addition of sarcosine N-carboxyanhydride (19.9 g, 172.9 mmol, 175 equiv.) followed by N,N-dimethylformamide (100 mL). The mixture was stirred for <30 seconds before the addition of neopentylamine (3.30 mL of 300 mM in DMF, 86.2 mg, 1 equiv.). The reaction vessel was wrapped in aluminum foil to prevent exposure to light. After 15-20 minutes, the reaction started to change from the initial clear and colorless solution to a light orange colored solution that continued to intensify in color as the reaction proceeded. IR was used to monitor the reaction progression via disappearance of the Sar NCA carbonyl stretches at approximately 1850 and 1778 cm$^{-1}$, with the latter being the preferred wave number to monitor. The reaction was approximately 90% done after 6 hours but was left to stir overnight. The next day, after a total of 19 hours, the reaction was complete. The circulating bath temperature was increased to 25° C. prior to the addition of D-leucine N-carboxyanhydride (4.66 g, 29.66 mmol, 30 equiv.) and L-tyrosine N-carboxyanhydride (4.10 g, 19.78 mmol, 20 equiv.). Additional DMF (approximately 5 mL) was used to rinse down the sides of the funnel and reaction vessel. Significant $CO_2$ gas formation was observed shortly after the reaction was initiated. IR was used to monitor the reaction progression via disappearance of the D-Leu NCA and L-Tyr NCA carbonyl stretches at approximately 1851 cm$^{-1}$ and 1785 cm$^{-1}$, with the latter being the preferred wave number to monitor. As the reaction proceeded, the color changed from a clear, bright orange to a clear, yellow-orange solution that was apparent after only a few hours. The reaction was >85% complete after 10 hours, and >99.9% complete after 24 hours. The reaction mixture (total of approximately 125 mL) was transferred to a beaker and fitted with an overhead stirrer. While vigorously stirring, ethyl acetate (250 mL, 2 volumes) was added to precipitate the product. The solids were collected via filtration into a medium fritted glass funnel. The solids were transferred back to the original precipitation beaker along with additional EtOAc (250 mL) and slurried with vigorous stirring for 20 minutes. The solids were collected in a new fritted glass funnel, and then the same 20 minutes slurrying procedure was repeated with EtOAc (250 mL) once more. The product was dried on the frit in a vacuum oven at 90-100° C. to yield 15.95 g (84.1%) of the title compound as a fine, off-white, dense powder. $^1$H NMR (DMSO-$d_6$) δ 9.2-8.9 (21H), 8.6-7.6 (39H), 7.2-6.4 (100H), 4.7-3.7 (694H), 3.1-2.6 (1039H), 1.9 (3H), 1.7-1.2 (33H), 1.0-0.6 (186H); GPC (DMF, 50 mM LiBr) Mn=16.9 kDa, Mp=18.0 kDa, PDI=1.08.

Preparation of $Sar_{175}$-b-p-[D-$Leu_{30}$-co-L-$Tyr_{20}$]-Ac (TFS-2-Ac). A round-bottomed flask was charged with TFS-2 (500 mg, 0.0261 mmol, 1 equiv.) and DMF (5.0 mL), and the mixture was stirred and heated with a heat gun to dissolve the material. Once the reaction mixture cooled to ambient temperature, triethylamine (36 μL, 0.261 mmol, 10 equiv.) and acetic anhydride (25 μL, 0.261 mmol, 10 equiv.) were added. The reaction was stirred for 24 hours before being transferred to a beaker using a minimum amount of N,N-dimethylformamide (approximately 1.5 mL) to assist in the transfer. With vigorous stirring, a large excess of ethyl acetate (40 mL) was added over 1 minute. The precipitation was stirred for 5 minutes before the solids were collected in a fritted glass funnel. The product was washed on the funnel with additional ethyl acetate (2×40 mL) and then dried at 95° C. for 48 hours to yield the title compound as a granular white powder (320 mg, 64.0%). $^1$H NMR (DMSO-$d_6$) δ 9.2-9.0 (16H), 8.8-7.5 (54H), 7.5-6.4 (100H), 4.7-3.7 (843H), 3.2-2.6 (1272H), 2.2 (24H), 1.8-1.0 (96H), 1.0-0.4 (211H).

Preparation of $Sar_{125}$-b-p-[D-$Leu_{20}$-co-L-$Tyr_{15}$] (BS-I-8). Following the general procedure of for TFS-1 with the following reagent equivalents and amounts: neopentylamine (30 mg, 1 equiv.), sarcosine NCA (4.95 g, 125 equiv.), D-Leu NCA (1.08 g, 20 equiv.), and L-Tyr (1.07 g, 15 equiv.) yielded the title compound as a light yellow solid (3.7 g, 79%). GPC (DMF, 50 mM LiBr) Mn=15.1 kDa, Mp=16.1 kDa, PDI=1.09.

Preparation of $Sar_{175}$-b-p-[D-Glu(OBn)$_{25}$-co-L-Glu(OBn)$_{25}$] (BS-I-9). Following the general procedure for TFS-1 with the following reagent equivalents and amounts: neopentylamine (43 mg, 1 equiv.), sarcosine NCA (10.0 g, 175 equiv.), D-Glu(OBn) NCA (3.27 g, 25 equiv.), and L-Glu(OBn) (3.27 g, 25 equiv.) yielded the title compound as a light yellow solid (10 g, 86%). GPC (DMF, 50 mM LiBr) Mn=15.9 kDa, Mp=16.9 kDa, PDI=1.06.

Preparation of $Sar_{175}$-b-p-[D-$Phe_{20}$-co-L-$Tyr_{20}$] (BS-I-10). Following the general procedure for TFS-1 with the following reagent equivalents and amounts: neopentylamine (43 mg, 1 equiv.), sarcosine NCA (10.0 g, 175 equiv.), D-Phe NCA (1.90 g, 20 equiv.), and L-Tyr (2.06 g, 20 equiv.) yielded the title compound as a light yellow solid (7.8 g, 85%). GPC (DMF, 50 mM LiBr) Mn=14.9 kDa, Mp=15.9 kDa, PDI=1.04.

Identification of TFRP-1. Each of the five selected polymers were initially formulated with 10% and 15% feed ratios of ixabepilone. Each of the tested polymers successfully encapsulated ixabepilone at 10% and 15% feed ratios. The feed ratios were thus increased to 20%, 25%, and 30%, and the formulation repeated with each polymer. BS-I-9 was unable to successfully encapsulate ixabepilone at feed ratios of 20%, 25% and 30%, and BS-I-8 and BS-I-10 were only able to successfully encapsulate ixabepilone at feed ratios of 20% and 25%. Each formulation was successful with polymers BS-I-11 and BS-I-12, so the feed ratio was increased to 35 and 40% for these polymers. Remarkably, both polymers successfully formulated 35% and 40% feed ratios of ixabepilone. Higher feed ratios were not attempted. Based upon the ability of BS-I-11 and BS-I-12 to successfully encapsulate ixabepilone at high feed ratios, these two polymers were selected for additional formulation work.

Formulations of BS-I-11 and BS-I-12 were prepared both with glycine and trehalose. Throughout the development process, no discernable difference between trehalose and glycine was observed.

Four separate formulations were advanced to an initial pharmacokinetic screening study. These formulations include the last four test articles in Table 1. The 20% feed ratio formulations were made with a 1:1 ratio of polymer to glycine, while the 4% feed ratio formulations were prepared with a 2:1 ratio of polymer to glycine.

Preparation of TFS-1 Drug Product with 20% Ixabepilone Feed. 500 mg of TFS-1 and 500 mg of glycine were dissolved in 38.3 mL of 30:70 (v/v) tert-butanol:water to produce a solution of 13.05 mg/mL of each component. The pH of the resulting solution was adjusted to pH 7.0 using 25 mM NaOH. Separately, ixabepilone (100 mg) was dissolved in 11.6 mL of 95:5 (v/v) tert-butanol:water with the assistance of a sonicating water bath, to produce a solution of 8.62 mg/mL. Both solutions were chilled to 4° C. and were kept cold during subsequent processing to prevent degradation of ixabepilone. The ixabepilone solution was added to the solution of polymer/glycine while stirring, and the mixture was stirred for approximately 1 minute before filtering through a 0.2-μm PVDF filter. The resulting solution was frozen at −80° C., covered to exclude light, and then lyophilized for 2 days to yield the drug product as a white fragmented cake containing 8.51% of ixabepilone by weight.

Preparation of TFS-2 Drug Product with 20% Ixabepilone Feed. 500 mg of TFS-2 and 500 mg of glycine were dissolved in 38.3 mL of 30:70 (v/v) tert-butanol:water to produce a solution of 13.05 mg/mL of each component. The pH of the resulting solution was adjusted to pH 7.0 using 25 mM NaOH. Separately, ixabepilone (100 mg) was dissolved in 11.6 mL of 95:5 (v/v) tert-butanol:water with the assistance of a sonicating water bath to produce a solution of 8.62 mg/mL. Both solutions were chilled to 4° C. and were kept cold during subsequent processing to prevent degradation of ixabepilone. The ixabepilone solution was added to the solution of polymer/glycine while stirring, and the mixture was stirred for approximately 1 minute before filtering through a 0.2-μm PVDF filter. The resulting solution was frozen at −80° C., covered to exclude light, and then lyophilized for 2 days to yield the drug product as a white fragmented cake containing 9.46% of ixabepilone by weight.

Preparation of TFS-1 Drug Product with 4% Ixabepilone Feed. 500 mg of TFS-1 and 250 mg of glycine were dissolved in 38 mL of 30:70 (v/v) tert-butanol:water to produce a solution of 13.2 mg/mL TFS-1 and 6.58 mg/mL glycine. The pH of the resulting solution was adjusted to pH 7.0 using 25 mM NaOH. Separately, ixabepilone (20 mg) was dissolved in 11.5 mL of 95:5 (v/v) tert-butanol:water with the assistance of a sonicating water bath to produce a solution of 1.74 mg/mL. Both solutions were chilled to 4° C. and were kept cold during subsequent processing to prevent degradation of ixabepilone. The ixabepilone solution was added to the solution of polymer/glycine while stirring, and the mixture was stirred for approximately 1 minute before filtering through a 0.2-μm PVDF filter. The resulting solution was frozen at −80° C., covered to exclude light, and then lyophilized for 2 days to yield the drug product as a white fragmented cake containing 2.76% of ixabepilone by weight.

Preparation of TFS-2 Drug Product with 4% Ixabepilone Feed. 500 mg of TFS-2 and 250 mg of glycine were dissolved in 38 mL of 30:70 (v/v) tert-butanol:water to produce a solution of 13.2 mg/mL TFS-2 and 6.58 mg/mL glycine. The pH of the resulting solution was adjusted to pH 7.0 using 25 mM NaOH. Separately, ixabepilone (20 mg) was dissolved in 11.5 mL of 95:5 (v/v) tert-butanol:water with the assistance of a sonicating water bath to produce a solution of 1.74 mg/mL. Both solutions were chilled to 4° C. and were kept cold during subsequent processing to prevent degradation of ixabepilone. The ixabepilone solution was added to the solution of polymer/glycine while stirring, and the mixture was stirred for approximately 1 minute before filtering through a 0.2-μm PVDF filter. The resulting solution was frozen at −80° C., covered to exclude light, and then lyophilized for 2 days to yield the drug product as a white fragmented cake containing 2.63% of ixabepilone by weight.

The formulation process was approximately 90% efficient (i.e., approximately 90% of the ixabepilone was recovered in the lyophilized powder). The formulation process did not adversely impact ixabepilone purity (99.6% pure before formulation, 98.8% after formulation, similar to IXEMPRA®).

The lyophilized powder is readily reconstituted in saline up to 100 mg/mL. Full dissolution is achieved in <30 seconds with mixing by hand. In addition, the resulting solution is stable at 4° C. for 24+ hours. The stability at room temperature is comparable to IXEMPRA®, with 6 hours of solution stability.

The stability of the lyophilized powder is under investigation at room temperature (21-22° C.), 4° C., and −20° C. No change was observed in the first two weeks.

In the initial pharmacokinetic screen, each of the four test articles described in Table 1 along with an IXEMPRA® control were administered to groups of rats comprising two male and two female Sprague-Dawley rats (Hilltop Lab Animals). IXEMPRA® was prepared by reconstituting ixabepilone in a solution of 20% PEG 300, 10% CREMOPHOR®, 10% ethanol and 60% 50 mM phosphate buffer (pH 7.4) at 3.35 mg/mL, and administering 2.0 mL/kg by fast bolus IV infusion over 1-2 minutes via the tail vein to deliver an ixabepilone dose of 6.7 mg/kg. Copolymer formulations were reconstituted in saline to provide an ixabepilone concentration of 1.34 mg/mL ixabepilone, and 5 mL/kg was administered by fast bolus IV infusion over 1-2 minutes via the tail vein to deliver a dose of ixabepilone of 6.7 mg/kg. Table 1 provides dosing information relating to the initial pharmacokinetic screen.

TABLE 1

| Test Article | Description | Dose (mg/kg) | Dose Volume (mL/kg) | Concentration (mg/mL) |
|---|---|---|---|---|
| Ixempra | Ixempra/PEG300 | 6.7 | 2 | 3.35 |
| KS-I-39 | BS-I-12, 20% | 6.7 | 5 | 1.34 |
| KS-I-41 | BS-I-12, 4% | 6.7 | 5 | 1.34 |
| KS-I-43 | BS-I-11, 20% | 6.7 | 5 | 1.34 |
| KS-I-45 | BS-I-11, 4% | 6.7 | 5 | 1.34 |

Figure 5:
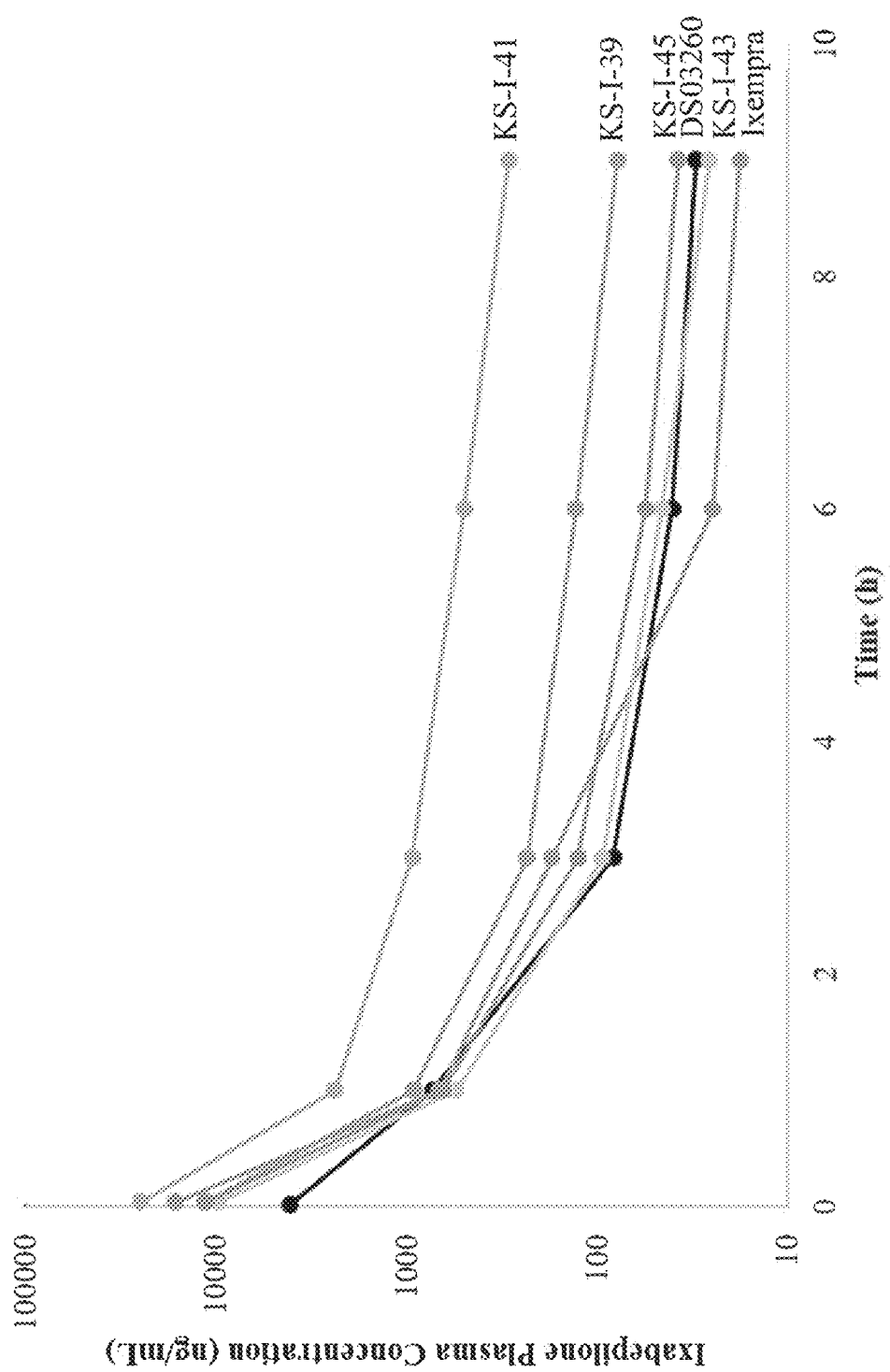
FIG. 5 is a graph of ixabepilone plasma concentration (ng/mL) versus time (h), and shows the pharmacokinetic profile of various formulations of ixabepilone described in Example 1.

Blood samples (approximately 300 μL) were collected from jugular veins into BD Microtainer tubes containing $K_2EDTA$ at the end of infusion (EOI), and after 1 hour, 3 hours, 6 hours, and 9 hours. The blood samples were centrifuged at 4° C., 3000 g for 15 minutes within 30 minutes of collection. Plasma was collected into polypropylene tubes or 96-well plates, quickly frozen on dry ice and stored at −70±10° C. until LC-MS/MS analysis. Quantification was determined by comparing a standard curve (of six non-zero concentrations) of ixabepilone in plasma against the samples from each time point. The concentration time curve for each formulation is shown in FIG. 5. This study design was replicated from a previous pharmacokinetic study of ixabepilone performed during the development of IXEMPRA® (Study number DS03260). Therefore, historical data from DS032060 is included as comparator data.

The area under the curve (AUC) was calculated using Excel, and is summarized in Table 2.

TABLE 2

| Test Article | AUC (ng*h/mL) |
|---|---|
| Ixempra - DS032060 | 5,051 |
| Ixempra | 7,183 |
| KS-I-39; BS-I-12, 20% feed | 8,224 |
| KS-I-41; BS-I-12, 4% feed | 21,196 |
| KS-I-43; BS-I-11, 20% feed | 5,860 |
| KS-I-45; BS-I-11, 4% feed | 6,925 |

Each of the formulations with 4% feed ixabepilone (i.e., higher polymer concentrations) exhibited higher plasma exposure levels than the formulations with 20% feed ixabepilone. It was also observed that formulations prepared with polymer BS-I-12 had higher exposures than formulations with BS-I-11. Without wishing to be bound by any particular theory, it is believed that this is related to the chain length of the polymers. BS-I-12 has a longer hydrophobic block, which likely resulted in a lower critical micelle concentration and a slightly more stable micelle. However, it was the 20% feed formulation with BS-I-11 that most resembled the IXEMPRA® concentration-time curves. Therefore, the formulation of 20% ixabepilone feed with BS-I-11 was established as the lead formulation candidate and named TFRP-1.

Example 2. TFRP-1 Drug Product Manufacturing Overview

Figure 4:
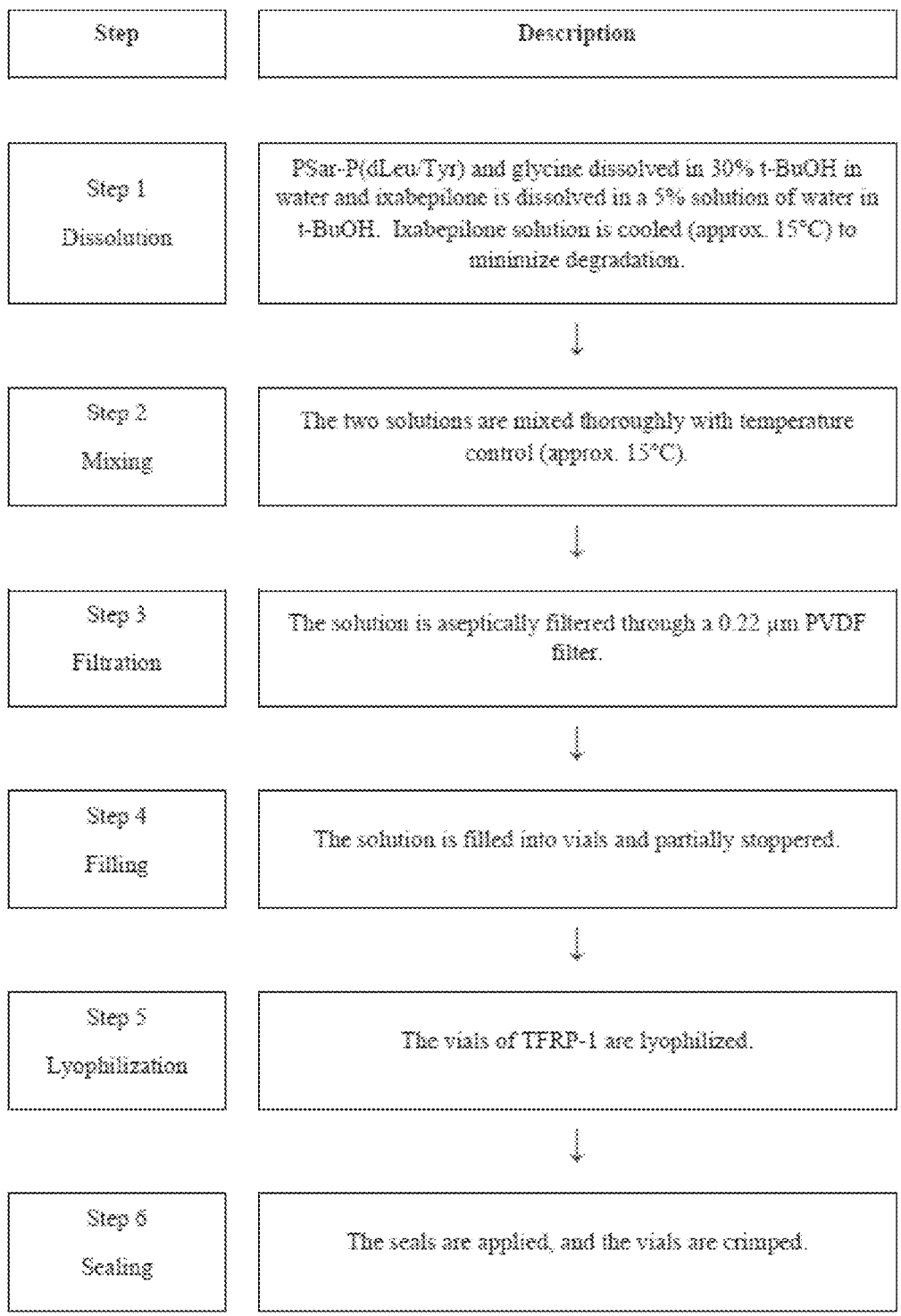
FIG. 4 is a flow chart, and depicts the manufacturing process of TFRP-1.

TFRP-1 is a formulation of ixabepilone comprising a polymer excipient, TFS-2, and a cryoprotectant, glycine. It was prepared by the dissolution of all components in a 45% solution of tert-butanol (t-BuOH) in water. Briefly, TFS-2 and glycine were dissolved (13.05 mg/mL for each component) in a solution of 30% t-BuOH in water, and ixabepilone was dissolved in a 5% solution of water in t-BuOH (8.62 mg/mL). The polymer solution was pH adjusted to approximately 7 with dilute sodium hydroxide, if required. All solutions were cooled (12-18° C.) to minimize degradation of ixabepilone. The two solutions were combined, mixed thoroughly, and filtered through a 0.22-μm poly(vinylindene fluoride) (PVDF) filter. The resulting solution was frozen and lyophilized to provide the TFRP-1 formulation. The lyophilized drug product is readily soluble in water and 0.9% saline. FIG. 4 is a flow chart depicting the manufacturing process of TFRP-1. The components and composition of the TFRP-1 drug product, based upon a 10-mL fill volume, are listed in Table 3.

TABLE 3

TFRP-1 Component Table

| Component | Unit Formulation (10 mL fill) |
|---|---|
| Ixabepilone | 20 mg |
| TFS-2 | 90 mg |
| Glycine | 90 mg |
| Tert-butanol | —[1] |
| Water for injection | —[1] |

[1]Removed during processing.

Example 3. Stability Study of TFRP-1

TFRP-1 will be placed on a stability study at the long-term storage condition (5±3° C.). The proposed long-term stability protocol is presented in Table 4.

TABLE 4

Long-term Stability Protocol for TFRP-1

| Test | Stability Interval (months) | | | | | | | | |
|---|---|---|---|---|---|---|---|---|---|
| | Initial | 1 | 3 | 6 | 9 | 12 | 18 | 24 | 36 |
| Physical appearance | x | x | x | x | x | x | x | x | x |
| Physical appearance reconstituted | x | x | x | x | x | x | x | x | x |
| pH of aqueous solution | x | x | x | x | x | x | x | x | x |
| Identification - Ixabepilone | x | x | x | x | x | x | x | x | x |
| Assay Ixabepilone | x | x | x | x | x | x | x | x | x |
| Related Substances - Ixabepilone | x | x | x | x | x | x | x | x | x |
| Identification - TFS-2 | x | x | x | x | x | x | x | x | x |
| Related Substances - TFS-2 | x | x | x | x | x | x | x | x | x |
| Water Content | x | x | x | x | x | x | x | x | x |
| Bioburden | x | | | | | x | x | x | x |
| Endotoxins | x | | | | | x | x | x | x | x = test

Example 4. Cytotoxicity of TFRP-1 in Two Human Cancer Cell Lines

The lung carcinoma cell line A549 and the breast cancer adenocarcinoma cell line MCF7 were treated with TFRP-1 at two doses, and compared to saline-treated control. The reported $IC_{50}$ dose in lung carcinoma cells for ixabepilone is between 2.3 nM and 19 nM, and the reported $IC_{50}$ dose in human breast cancer cell lines is between 1.4 nM and 45.9 nM.

A549 cells were treated with 2 nM or 20 nM TFRP-1. MCF7 cells were treated with 20 nM or 40 nM TFRP-1. After 96 hours of treatment, cells were counted for viability. Saline-treated A549 cells had an average viability count of $375.0 \times 10^4$. A549 cells treated with 2 nM TFRP-1 had a viability count of $181.0 \times 10^4$, and A549 cells treated with 20 nM TFRP-1 had a viability count of $69 \times 10^4$. Saline-treated MCF7 cells had an average viability count of $550.0 \times 10^4$. MCF7 cells treated with 20 nM TFRP-1 had a viability count of $287.0 \times 10^4$, and MCF7 cells treated with 40 nM TFRP-1 had a viability count of $62.5 \times 10^4$. It was determined that TFRP-1 demonstrated an equivalent pharmacological effect as free ixabepilone.

Materials and Methods

Cells: ATCC CCL-185 A549 Human Lung Carcinoma LOT #: 70018877; ATCC HTB-22 MCF7 Human Breast Adenocarcinoma LOT #: 70019550.

Materials and Equipment: Eagle's Minimum Essential Media (ATCC No. 30-2003); F-12K Media (ATCC No. 30-2008); Fetal Bovine Serum (ATCC No. 30-2020); Penicillin/Streptomycin (Thermo Fisher No. 15-140-122); Human Recombinant Insulin 0.01 mg/mL (Sigma No. 19278); Trypsin (ATCC No. 25-200-072); Phosphate Buffered Saline (Corning from Thermo Fisher No. 21040CM); Hemocytometer (Hausser from Fischer No. 02-671-6); Trypan blue (Gibco No. 15250061); p100 tissue culture dishes (Falcon-Corning No. 08-772E). Ixabepilone (Lot 3L7304N) was provided by R-Pharm US. TFRP-1 was prepared by Tyndall Formulation Services using a 20% feed ratio of ixabepilone with TFS-2. Saline control was phosphate-buffered 150 mM NaCl solution.

Experimental Procedure

Cells were rapidly thawed in a water bath at 37° C. and resuspended in appropriate media before being transferred to 60 mm or 100 mm tissue culture dishes. A549 cells were maintained in F12-K media, supplemented with 10% fetal bovine serum, and 1% penicillin/streptomycin. MCF7 cells were maintained in Eagle's Minimum Essential media, supplemented with 10% fetal bovine serum, 1% penicillin/streptomycin, and 0.01 mg/mL insulin. All cells were passaged at least three times before treatment. After 24 h of incubation, dishes were treated with saline control or TFRP-1. Saline was administered at the equivalent volume used for the ixabepilone treatment for each respective cell line. At 96 h, cells were trypsinized and harvested and counted with trypan blue on a hemocytometer.

Results

A549 cells were treated with saline, 20 nM ixabepilone, or 2 nM or 20 nM TFRP-1. 96 h after treatment, cells were counted. All cells were in log phase. The average cell viability count for treatment of saline control was $375 \times 10^4$. The average cell viability count for treatment of 20 nM ixabepilone treatment was $106 \times 10^4$ (n=3). The average viability cell count for treatment of 2 nM TFRP-1 was $181 \times 10^4$. The average cell viability count for treatment of 20 nM TFRP-1 was $69 \times 10^4$ (n=3). MCF7 cells were treated with saline, 40 nM ixabepilone, 20 nM TFRP-1 or 40 nM TFRP-1. The average cell viability count for treatment of saline control was $550 \times 10^4$. The average cell viability count for 40 nM ixabepilone was $70 \times 10^4$ (n=3). The average cell viability count for treatment of 20 nM TFRP-1 was $287 \times 10^4$. The average cell viability count for treatment of 40 nM TFRP-1 was $63 \times 10^4$ (n=3).

Conclusion

TFRP-1 demonstrated an equivalent pharmacological effect as free ixabepilone.

Example 5. Single-Dose Pharmacokinetics of Ixabepilone in Rats

The objective of this non-GLP study was to evaluate the pharmacokinetic profile of TFRP-1 compared to IXEMPRA®. Two groups of two Sprague-Dawley rats/sex/group were administered a single IV dose of either TFRP-1 or IXEMPRA®. Each dose was chosen such that all animals received 6.7 mg/kg of ixabepilone. The injection volume was 2 mL/kg for IXEMPRA® and 5 mL/kg for TFRP-1. Test articles were administered as a fast bolus via tail vein. The study design replicated a previous pharmacokinetic study of ixabepilone performed during the development of IXEMPRA®, Study No. D503260).

Blood samples from each rat were collected at the end of infusion, and 1, 3, 6, and 9 hours post infusion. The blood samples were processed to plasma and stored at −78° C. until analysis by liquid chromatography-mass spectrometry (LC-MS). The lower limit of quantification was 1.0 ng/mL.

The mean ixabepilone plasma concentration-time curves following a single IV dose of IXEMPRA® and TFRP-1 are shown in FIG. 1. Data from Study No. DS03260 is presented as comparator data. The area under the curve (AUC) values for each formulation were 5,051; 7,183; and 5,860 ng*h/mL for IXEMPRA® from D503260, IXEMPRA®, and TFRP-1, respectively. The results of this study indicate that the pharmacokinetic parameters for ixabepilone from IXEMPRA® and TFRP-1 are comparable.

Example 6. Repeat Dose Toxicity Study in Mice (Study 2019-05)

The purpose of this non-GLP study was to assess the tolerability of TFS-2 in healthy mice. Groups consisted of four female CD-1 mice per group. Group 1 was administered saline as a control. Groups 2-4 were administered TFS-2 by fast bolus IV via lateral tail vein. A dosing summary is provided in Table 5. Test article administration was on Day 1 and Day 8. The animals were observed at least once daily for mortality and signs of moribundity. Body weight was measured at least three times weekly. All animals were sacrificed on Day 15.

TABLE 5

Dosing Summary for Study 2019 May

| Group | Dose TFS-2 (mg/kg/dose) | Volume (mL/kg) | Conc. TFS-2 (mg/mL) | F |
|---|---|---|---|---|
| 1 | 0 | 10 | 0 | 4 |
| 2 | 500 | 10 | 50 | 4 |
| 3 | 1000 | 10 | 100 | 4 |
| 4 | 1,500 | 10 | 150 | 4 |

Figure 2:
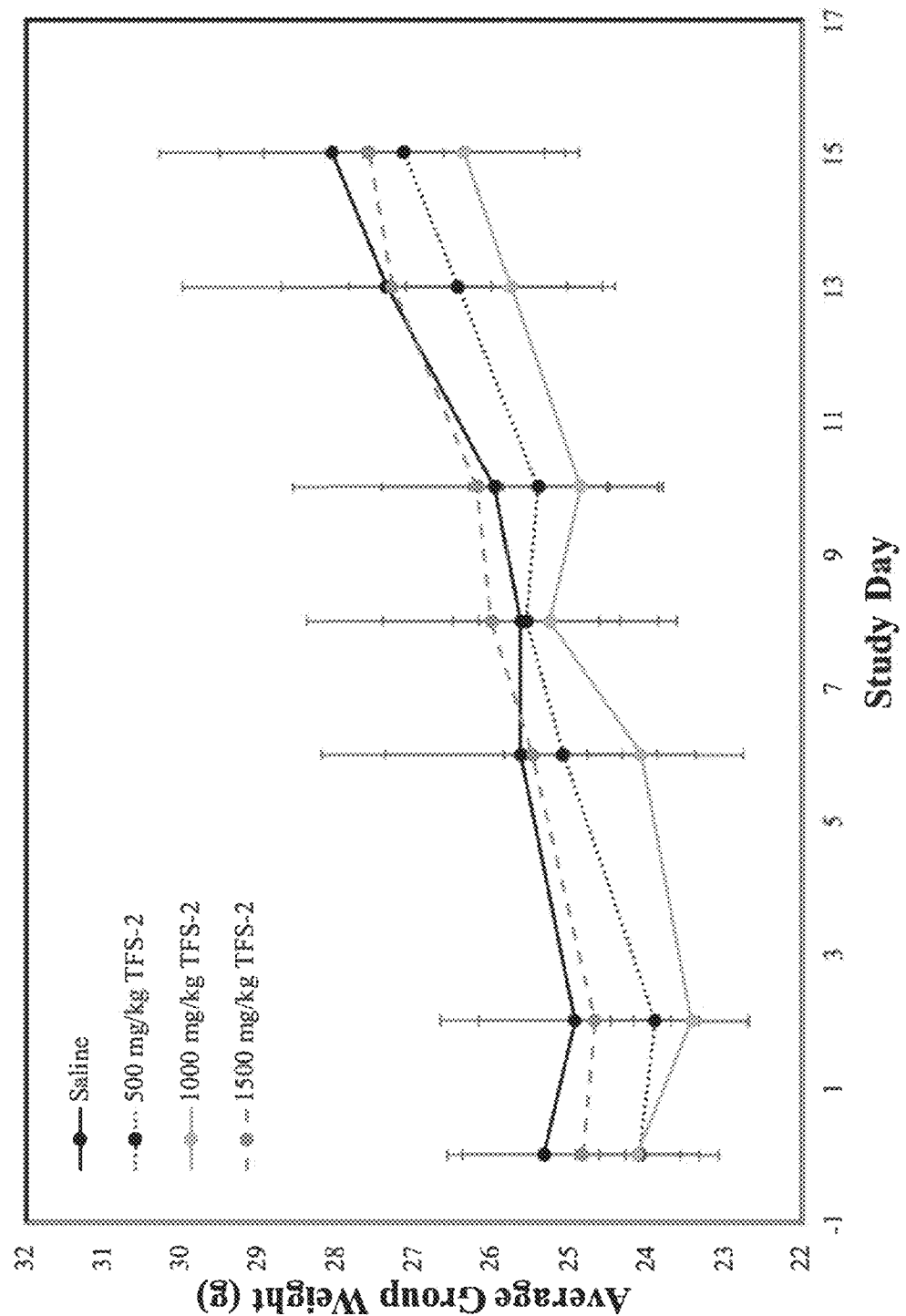
FIG. 2 is a graph of average group weight (g) versus study day, and shows the average mouse group growth for Study 2019-05.

The average weight of each group over the two-week study is shown in FIG. 2. The average growth rate for each group is shown in Table 6. TFS-2 did not alter growth rate, even in the high-dose group that received 1,500 mg/kg. Complete blood count (CBC) analysis was performed on a terminal blood draw for each group. Minor and not statistically significant changes were observed for red blood cell (RBC) counts, white blood cell (WBC) counts, and platelets for the groups treated with TFS-2. No other changes in the CBC were noted. It was determined that TFS-2 was well tolerated by mice at doses as high as 1,500 mg/kg.

TABLE 6

Mouse Average Growth Rates for Study 2019 May

| Group | Starting Mass (g) | Final Mass (g) | Mass Grown (g) | % growth |
|---|---|---|---|---|
| Saline Control | 25.3 | 28.1 | 2.7 | 10.8% |
| 500 mg/kg TFS-2 | 24.1 | 27.1 | 3.0 | 12.6% |
| 1000 mg/kg TFS-2 | 24.1 | 26.4 | 2.2 | 9.2% |
| 1500 mg/kg TFS-2 | 24.8 | 27.6 | 2.8 | 11.1% |

Example 7. Repeat Dose Toxicity Study in Rats (Study 2019-04)

The purpose of this non-GLP study was to assess the tolerability of TFS-2 in healthy rats. Each group consisted of four female Sprague-Dawley rats. Group 1 was administered saline as a control. Groups 2-4 were administered TFS-2 via fast bolus IV infusion. A dosing summary is provided in Table 7. Test articles were administered on Day 1 and Day 8. The animals were observed at least once daily for mortality and signs of moribundity. Body weight was measured at least 3 times weekly. All animals were sacrificed on Day 15.

TABLE 7

Dosing Summary for Study 2019 April

| Group | Dose TFS-2 (mg/kg/dose) | Volume (mL/kg) | Conc. TFS-2 (mg/mL) | F |
|---|---|---|---|---|
| 1 | 0 | 10 | 0 | 4 |
| 2 | 500 | 10 | 50 | 4 |
| 3 | 1000 | 10 | 100 | 4 |
| 4 | 1,500 | 10 | 150 | 4 |

Figure 3:
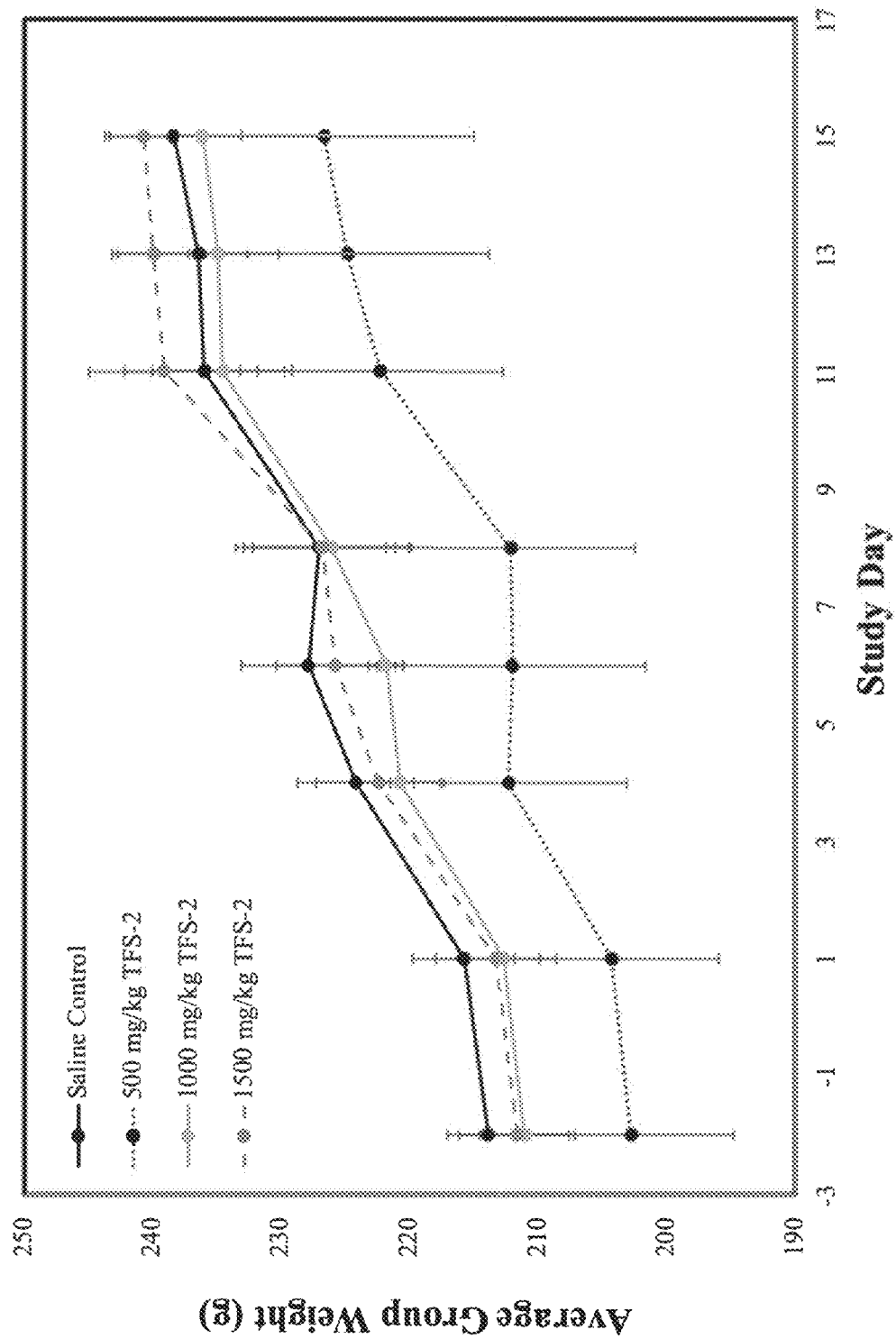
FIG. 3 is a graph of average group weight (g) versus study day, and shows the average rat group growth for Study 2019-04.

The average weight of each group over the two-week study is shown in FIG. 3. The average growth rate for each group is shown in Table 8. TFS-2 did not alter growth rate compared to control in any treatment group. CBC analysis was performed on a terminal blood draw for each group. Minor and not statistically significant changes were observed for WBC and platelets for the groups treated with TFS-2. No other changes in the CBC were noted. It was determined that TFS-2 was well tolerated by rats at doses as high as 1,500 mg/kg.

TABLE 8

Rat Average Group Growth Rates for Study 2019 April

| Group | Starting Mass (g) | Final Mass (g) | Mass Grown (g) | % growth |
|---|---|---|---|---|
| Saline Control | 213.9 | 238.4 | 24.5 | 11.4% |
| 500 mg/kg TFS-2 | 202.8 | 226.6 | 23.8 | 11.7% |
| 1000 mg/kg TFS-2 | 211.1 | 236.1 | 25.1 | 11.9% |
| 1500 mg/kg TFS-2 | 211.6 | 240.7 | 29.1 | 13.8% |

Example 8. One-month Repeat Dose (QWx5) Intravenous Toxicity Study in Rats

This GLP study was designed to assess the toxicity and toxicokinetic profile of TFRP-1 when administered to rats once weekly for five weeks via a slow bolus IV infusion (at least 1 minute), and to evaluate recovery during a 1-month, drug-free period. More specifically, the study was a 32-day intravenous injection toxicity and toxicokinetics study in rats with 28-day recovery period. This study was designed to replicate a previous GLP study (Study Number D503127) performed during the development of IXEMPRA®.

Protocol

Two hundred and twenty (110/sex) rats were randomly assigned to six groups (three TFRP-1 groups, one vehicle control group [saline], one formulation control group [TFS-2], and one ixabepilone reference control group [IXEMPRA®]) to determine the toxicity of TFRP-1 when administered by intravenous injection once weekly (on Days 1, 8, 15, 22, and 29) for a total of 5 administrations. Animals were randomly assigned to groups by Provantis based on body weight. The last five Main Study animals/sex from all three control groups and the TFRP-1 high-dose group were allocated for recovery. The study design is summarized in the tables below. The dosing summary and animal assignment are shown in Tables 9 and 10, respectively.

dose formulations precipitated when stored in a 2° C. to 8° C. refrigerator or with ice packs, dose formulations were re-prepared for Group 3 and storage conditions were changed to room temperature. Therefore, Group 3 was dosed three days later than other groups. The dosage volume was calculated based on the most recent scheduled animal body

TABLE 9

Dosing Summary for Intravenous Toxicity Study

| | | Weekly Doses[a] | | | | | |
|---|---|---|---|---|---|---|---|
| | | Ixabepilone | | TFRP-1 | | TFS-2 | |
| Group/ Color | Volume (mL/kg) | Dose (mg/kg) | Conc. (mg/mL) | Dose (mg/kg) | Conc. (mg/mL) | Dose (mg/kg) | Conc. (mg/mL) |
| 1[b]/White | 2 | 0 | 0 | 0 | 0 | 0 | 0 |
| 2[c]/Magenta | 2 | 0 | 0 | 0 | 0 | 10.0 | 5.0 |
| 3[d]/Blue | 2 | 2 | 1.0 | 0 | 0 | 0 | 0 |
| 4[e]/Green | 2 | 0.1 | 0.05 | 1.1 | 0.56 | 0.5 | 0.25 |
| 5[e]/Yellow | 2 | 1 | 0.5 | 11.1 | 5.6 | 5.0 | 2.5 |
| 6[e]/Red | 2 | 2 | 1.0 | 22.2 | 11.1 | 10.0 | 5.0 |

Conc. = Concentration
[a]Doses represented active ingredient.
[b]Saline (vehicle) control group
[c]Formulation control group (TFS-2)
[d]Ixabepilone positive control group
[e]TFRP-1 is 9.0% ixabepilone. Therefore, a 1 mg/mL ixabepilone solution is equivalent to 11.1 mg/mL TFRP-1.

TABLE 10

Animal Assignment for Intravenous Toxicity Study

| | Numbering of Main Study Animals | | | | Numbering of TK Animals | |
|---|---|---|---|---|---|---|
| | Dosing Phase | | Recovery Phase | | | |
| Group/ Color | Males | Females | Males | Females | Males | Females |
| 1[a]/White | 1001-1010 | 1501-1510 | 1011-1015 | 1511-1515 | 1016-1018 | 1516-1518 |
| 2[b]/Magenta | 2001-2010 | 2501-2510 | 2011-2015 | 2511-2515 | 2016-2018 | 2516-2518 |
| 3[c]/Blue | 3001-3010 | 3501-3510 | 3011-3015 | 3511-3515 | 3016-3021 | 3516-3521 |
| 4[d]/Green | 4001-4010 | 4501-4510 | NA | NA | 4011-4016 | 4511-4516 |
| 5[d]/Yellow | 5001-5010 | 5501-5510 | NA | NA | 5011-5016 | 5511-5516 |
| 6[d]/Red | 6001-6010 | 6501-6510 | 6011-6015 | 6511-6515 | 6016-6021 | 6516-6521 |

TK = toxicokinetics.
[a]Saline (vehicle) control group
[b]Formulation control group (TFS-2)
[c]Ixabepilone positive control group
[d]TFRP-1 is 9.0% ixabepilone. Therefore, a 1 mg/mL ixabepilone solution is equivalent to 11.1 mg/mL TFRP-1

Dosages were selected based on the data from a one month intermittent-dose (QWx5) intravenous toxicity study in rats with BMS-247550 (ixabepilone) (BMS Study No. DS03127). In that study, weekly intravenous dosing with BMS-247550 for one month (5 doses) was generally well tolerated in rats at doses of 0.1, 1.0 or 2.0 mg/kg. The no observed adverse effect level (NOAEL) was considered to be 0.1 mg/kg. The major effects noted at doses of 1.0 and 2.0 mg/kg were consistent with those of other microtubule-stabilizing anticancer agents and included reversible hematopoietic/lymphoid and gastrointestinal (including hepatic) toxicities, peripheral neuropathy, and delayed testicular toxicity. The same ixabepilone-equivalent dose levels were selected in the current study to compare safety of TFRP-1 to ixabepilone.

Vehicle and dose formulations were administered once weekly for up to 5 doses by a bolus intravenous injection (1 to 2 minutes) via a tail vein. The first day of dosing was designated as Day 1. Because the initially prepared Group 3 weights. The TFRP-1 and TFS-2 formulations intended for dosing were placed at room temperature for more than 30 minutes before dosing and used within 2 hours after being placed at room temperature. The ixabepilone dose formulations were used within 6 hours after preparation. All dose levels in this Example refer to dose of ixabepilone.

Clinical Observations

No treatment-related clinical signs were noted in animals given the formulation control TFS-2 (Group 2) or the low or mid-dose TFRP-1 (Groups 4 and 5, 0.1 and 1 mg/kg/dose ixabepilone).

Test-related clinical signs were noted in females given the high-dose TFRP-1 (Group 6, 2 mg/kg/dose ixabepilone). Such clinical signs, in the order of most frequent to less frequent, included unkempt and thin appearance (first observed on Day 6), abnormal stool (soft and/or yellow, first observed on Day 11), hunched posture (first observed on Day 5), soiled coat (yellow, anogenital region, first observed on Day 5) which was likely due to contamination from the abnormal soft stool, abnormal gait (first observed on Day 19), decreased activity (first observed on Day 5), skin discolored (ears/bilateral/pale, first observed on Day 6) and coldness to touch (first observed on Day 13). These clinical signs were no longer observed during the recovery phase in the high-dose TFRP-1 group. Most of the above clinical signs (unkempt and thin appearance, abnormal stool, hunched posture, and abnormal gait) were also noted in females given the reference control IXEMPRA® (Group 3, 2 mg/kg/dose ixabepilone) with similar frequency during the dosing phase. Into the recovery phase, unkempt and thin appearance was still noted in 1 or 2 females in the IXEMPRA® group. These females were recovered after Day 38.

Clinical signs observed only in the reference control IXEMPRA® (Group 3, 2 mg/kg/dose ixabepilone) males and/or females included scab, firm area, swelling, and desquamation of the tail (base or middle, first observed on Day 8). These findings suggested treatment-related effects at the injection sites and correlated microscopically with perivascular fibrosis, and focal erosion/ulceration and hyperkeratosis. At the end of the recovery phase, firm area and/or desquamation of the tail were still noted in a few females, however, without microscopic correlates. All other clinical signs observed were considered incidental and unrelated to treatments, as they were of the types seen in untreated rats in this laboratory, of isolated occurrence, or also observed in the saline control group.

Body Weights

No treatment-related changes in body weight were noted in animals given the formulation control TFS-2 (Group 2) or the low-dose TFRP-1 (Group 4, 0.1 mg/kg/dose Ixabepilone). Decreased body weight or body weight gain was noted in males and females given the mid- and high-dose TFRP-1 (Groups 5 and 6, 1 and 2 mg/kg/dose ixabepilone) and the reference control IXEMPRA® (Group 3, 2 mg/kg/dose ixabepilone), and correlated with decreased food consumption. The decreases in body weight were similar between the 2 mg/kg/dose TFRP-1 and IXEMPRA® groups, although the IXEMPRA® group had a slightly higher mean baseline body weight due to late initiation of dosing. During the dosing phase, body weights decreased up to −22%/−22% (males/females) for the 2 mg/kg/dose TFRP-1 group and up to −23%/−21% (males/females) for the 2 mg/kg/dose IXEMPRA® group, respectively, relative to the saline control (Group 1). In animals given 1 mg/kg/dose TFRP-1 (Group 5), body weights decreased up to −10% in the males and up to −13% in the females, relative to the saline control (Group 1). The effects on body weight changes were primarily seen in the early phase of each dosing cycle. In the later period of the non-dosing days of each dosing cycle, body weight gains tended to increase to a level comparable or close to that of the saline control. Into the recovery phase, decreased body weight or body weight gain was noted in the first week in the males and females previously given the high-dose TFRP-1 (Group 6, 2 mg/kg/dose ixabepilone) and the reference control IXEMPRA® (Group 3, 2 mg/kg/dose ixabepilone). Body weight gains were greater than or comparable to that of the saline control (Group 1) during the remaining period of the recovery phase. By the end of the recovery phase, the group mean body weights were −17%/−9% (males/females) and −20%/−8% (males/females) lower relative to the saline controls (Group 1) by Day 59, for the 2 mg/kg/dose TFRP-1 and IXEMPRA® groups respectively.

Food Consumption

No treatment-related changes in food consumption were noted in animals given the formulation control TFS-2 (Group 2) or the low-dose TFRP-1 (Group 4, 0.1 mg/kg/dose Ixabepilone). Decreased food consumption was noted in males and females given the mid- and high-dose TFRP-1 (Groups 5 and 6, 1 and 2 mg/kg/dose ixabepilone) and the reference control IXEMPRA® (Group 3, 2 mg/kg/dose Ixabepilone). The decreases in food consumption were similar between the 2 mg/kg/dose TFRP-1 and IXEMPRA® groups. During the dosing phase, food consumptions decreased up to −25%/−38% (males/females) for the 2 mg/kg/dose TFRP-1 group and up to −28%/−35% (males/females) for the 2 mg/kg/dose IXEMPRA® group, respectively, relative to the saline control (Group 1). In animals given 1 mg/kg/dose TFRP-1 (Group 5), food consumptions decreased up to −15% for both males and females, relative to the saline control (Group 1).

Into the recovery phase, decreased food consumption was noted in the first week in the males and females previously given the high-dose TFRP-1 (Group 6, 2 mg/kg/dose ixabepilone) and the reference control IXEMPRA® (Group 3, 2 mg/kg/dose ixabepilone). The food consumptions were greater than or comparable to that of the saline control (Group 1) during the remaining period of the recovery phase.

Ophthalmology Examinations

No treatment-related ophthalmologic changes were noted during the dosing and recovery phase exams in animals given TFRP-1, the formulation control TFS-2, or the reference control IXEMPRA®. All ocular findings in the pretest, dosing and recovery phases were considered common background or spontaneous findings consistent with the age and strain of this species.

Hematology

No treatment-related changes in hematology were noted in animals given the formulation control TFS-2 (Group 2) or the low-dose TFRP-1 (Group 4, 0.1 mg/kg/dose ixabepilone). Treatment-related changes in hematology were noted in males and females given the mid- and high-dose TFRP-1 (Groups 5 and 6, 1 and 2 mg/kg/dose ixabepilone) and the reference control IXEMPRA® (Group 3, 2 mg/kg/dose ixabepilone). Changes were similar between the 2 mg/kg/dose TFRP-1 and IXEMPRA® groups. Decreased circulating red blood cell mass (erythrocytes, hemoglobin, and hematocrit) and reticulocytes were noted in males and females given 2 mg/kg/dose IXEMPRA® or 1 or 2 mg/kg/dose TFRP-1 on Day 32. These changes correlated with decreased hematopoietic cellularity in the sternal bone marrow of these animals. Erythrocytes were also observed with increases in mean corpuscular volume and mean corpuscular hemoglobin at 2 mg/kg/dose and increase in RBC distribution width at >1 mg/kg/dose. Decreased leukocytes including lymphocytes, monocytes and eosinophils were noted in males and females given 2 mg/kg/dose IXEMPRA® or 1 or 2 mg/kg/dose TFRP-1 on Day 32. These changes correlated with decreased hematopoietic cellularity and decreased lymphocyte cellularity observed in the in the sternal bone marrow and lymphoid tissues (thymic cortex, spleen and mandibular and mesenteric lymph nodes) in these animals. Increased neutrophils were noted in males and females given 2 mg/kg/dose IXEMPRA® and TFRP-1 on Day 32. These changes were interpreted as non-specific responses to stress associated with toxicity observed clinically at this dose level.

Decreased platelet and increased mean platelet volume were noted in males and females given 2 mg/kg/dose IXEMPRA® or 1 or 2 mg/kg/dose TFRP-1 on Day 32. These changes correlated with decreased hematopoietic cellularity in the sternal bone marrow of these animals.

By the end of the recovery phase on Day 60, most hematology data returned to levels comparable to the saline control with the exceptions that increased hematocrits, mean corpuscular volume and mean corpuscular hemoglobin were still noted in animals previously given 2 mg/kg/dose IXEMPRA® and TFRP-1, and decreased mean corpuscular hemoglobin concentration and reticulocytes were noted in animals previously given 2 mg/kg/dose IXEMPRA®. These may suggest active hematopoietic regeneration as indicated by the partial reversal of microscopic findings of the sternal bone marrow following the completion of the recovery phase.

Noteworthy hematology findings are summarized in Tables 11A and 11B below. Noteworthy findings were characterized by their differences relative to the saline control animals and reference data, as appropriate.

TABLE 11A

Treatment-Related Changes in Hematology (Percent Difference in Mean Values from Concurrent Saline Control)[a]

| Doses (mg/kg/dose) | 0 | | 2 | | 1 | | 2 | |
|---|---|---|---|---|---|---|---|---|
| Test or Control Article | Saline | | Ixempra | | TFRP-1 | | TFRP-1 | |
| Sex | M | F | M | F | M | F | M | F |
| Day 32 - Dosing Phase (No. Animals) | 10 | 10 | 10 | 10 | 10 | 9 | 10 | 8 |
| Erythrocytes ($10^6$ µL) | 7.55 | 7.08 | −9%*** | −14%*** | −3% | −4% | −10%*** | −13%*** |
| Hemoglobin (g/dL) | 14.3 | 13.5 | −5% | −10%*** | −3% | −5% | −4% | −9%** |
| Hematocrits (%) | 43.2 | 39.8 | −6%* | −9%** | −3% | −4% | −6%* | −8%* |
| Mean Corpuscular Volume (fL) | 57.4 | 56.3 | +3%* | +6%*** | — | — | +5%** | +6%*** |
| Mean Corpuscular Hemoglobin (pg) | 19.0 | 19.1 | +4%** | +6%*** | — | — | +6%*** | +5%** |
| RBC Distribution Width (%) | 12.4 | 12.3 | +24%*** | +50%*** | +7%*** | +8% | +31%*** | +54%*** |
| Reticulocytes ($10^9$/L) | 215.5 | 201.7 | −93%*** | −88%*** | −71%*** | −86% | −93% | −80%*** |
| Leukocytes ($10^3$/µL) | 7.01 | 6.13 | −24% | −52%*** | −16% | −24% | −39%** | −45%** |
| Neutrophils ($10^3$/µL) | 0.76 | 0.60 | +143%* | +17% | — | — | +57% | +7% |
| Lymphocytes ($10^3$/µL) | 6.01 | 5.34 | −43%** | −59% | −15% | −21% | −50% | −50%** |

TABLE 11B

Treatment-Related Changes in Hematology (Percent Difference in Mean Values from Concurrent Saline Control)[a]

| Doses (mg/kg/dose) | 0 | | 2 | | 1 | | 2 | |
|---|---|---|---|---|---|---|---|---|
| Test or Control Article | Saline | | Ixempra | | TFRP-1 | | TFRP-1 | |
| Sex | M | F | M | F | M | F | M | F |
| | | | *** | | | | *** | |
| Monocytes ($10^3$/µL) | 0.14 | 0.09 | −51%** | −55%** | −61%** | −64%*** | −64%*** | −54%* |
| Eosinophils ($10^3$/µL) | 0.05 | 0.06 | −69%*** | −92%*** | −46%** | −60%*** | −85%*** | −100%*** |
| Platelet ($10^3$/µL) | 1017 | 1088 | −3% | −17% | −2% | −10% | −2% | −9% |
| Mean Platelet Volume (fL) | 8.8 | 8.8 | +6% | +19%*** | +8% | +7% | +16%*** | +23%*** |
| Day 60 - Recovery Phase (No. Animals) | 5 | 4 | 5 | 5 | NA | NA | 5 | 5 |
| Hematocrits (%) | 41.8 | 39.9 | +10%*** | +13%*** | NA | NA | +6%* | +7%* |
| Mean Corpuscular Volume (fL) | 53.1 | 55.4 | +12%*** | +11%** | NA | NA | +11%*** | +11%** |
| Mean Corpuscular Hemoglobin (pg) | 17.8 | 18.9 | +5% | +7% | NA | NA | +9%** | +10%* |
| Mean Corpuscular Hemoglobin Conc. (g/dL) | 33.5 | 34.0 | −6%*** | −4%** | NA | NA | — | — |
| Reticulocytes ($10^9$/L) | — | 189.8 | −36%* | NA | NA | | — | −22% |

[a]For controls, group means are shown. For treated groups, percent differences from saline control are shown.
Statistically significantly different from concurrent controls (saline): *$p \leq 0.05$, $p \leq 0.01$, *$p \leq 0.001$.
A dash (—) indicates no test article treatment-related change in this group or not applicable.
M = Males, F = Females All other differences observed in hematological parameters, including those that were of statistical significance, were considered incidental and unrelated to treatment because they were small in magnitude, not dose-related, and/or within the historical reference ranges of this laboratory.

Coagulation

No treatment-related changes in coagulation were noted in animals given TFRP-1, the formulation control TFS-2, or the reference control IXEMPRA®. All differences observed in coagulation parameters were considered incidental and unrelated to the treatment because they were small in magnitude, not dose-related, and/or within the historical reference ranges of this laboratory.

Serum Chemistry

No treatment-related changes in serum chemistry were noted in animals given the formulation control TFS-2

Decreased total protein including albumin and globulin and increased triglyceride were noted in females given 2 mg/kg/dose IXEMPRA® and 2 mg/kg/dose TFRP-1.

Decreased potassium and increased sodium and chloride were noted in males given 2 mg/kg/dose IXEMPRA®.

By the end of the recovery phase on Day 60, most serum chemistry data returned to levels comparable to the saline control with the exceptions that increased alanine aminotransferase, aspartate aminotransferase, and triglyceride were still noted in females previously given 2 mg/kg/dose IXEMPRA® and TFRP-1. However, these were not accompanied by microscopic changes of hepatic injuries.

Noteworthy serum chemistry findings are summarized in Table 12 below. Noteworthy findings were characterized by their differences relative to the saline control animals and reference data, as appropriate.

TABLE 12

Treatment-Related Changes in Serum Chemistry (Percent Difference in Mean Values from Concurrent Saline Control)[a]

| Doses (mg/kg/dose) | | | | | | | | |
|---|---|---|---|---|---|---|---|---|
| | 0 | | 2 | | 1 | | 2 | |
| Test Article | | | | | | | | |
| | Saline | | Ixempra | | TFRP-1 | | TFRP-1 | |
| Sex | | | | | | | | |
| | M | F | M | F | M | F | M | F |
| Day 32 - Dosing Phase (No. Animals) | 10 | 10 | 10 | 10 | 10 | 10 | 10 | 8 |
| Alanine Aminotransferase (U/L) | 32 | 24 | +161% | +114%*** | — | +54% | +150%* | +295%*** |
| Aspartate Aminotransferase (U/L) | 126 | 122 | +73% | +44% | — | +50% | +53% | +100%*** |
| Total Bilirubin (µmol/L) | 2.09 | 2.69 | +43%* | +20% | +11% | +32% | +39%* | +62% |
| Total Cholesterol (mmol/L) | 1.73 | 1.34 | +33%** | +103%*** | — | +65%** | +52%*** | +134%*** |
| Total Protein (g/L) | — | 63.1 | — | −8%* | — | — | — | −9%* |
| Albumin (g/L) | — | 36.8 | — | −9%* | — | — | — | −12%** |
| Globulin (g/L) | — | 26.4 | — | −7% | — | — | — | −5% |
| Tryglyceride (mmol/L) | — | 0.28 | — | +52%** | — | — | — | +76%*** |
| Potassium (mmol/L) | 5.0 | — | −8%* | — | — | — | — | — |
| Sodium (mmol/L) | 143 | — | +2%*** | — | — | — | — | — |
| Chloride (mmol/L) | 103 | — | +3%*** | — | — | — | — | — |
| Day 60 - Recovery Phase (No. Animals) | 5 | 5 | 5 | 5 | NA | NA | 5 | 5 |
| Alanine Aminotransferase (U/L) | — | 29 | — | +62% | NA | NA | — | +131% |
| Aspartate Aminotransferase (U/L) | — | 136 | — | +47% | NA | NA | — | +82% |
| Tryglyceride (mmol/L) | — | 0.40 | — | +30% | NA | NA | — | +46% |

[a]For controls, group means are shown. For treated groups, percent differences from saline control are shown.
Statistically significantly different from concurrent controls (saline): *p ≤ 0.05, p ≤ 0.01, *p ≤ 0.001.
A dash (—) indicates no test article treatment-related change in this group or not applicable.
M = Males, F = Females (Group 2) or the low-dose TFRP-1 (Group 4, 0.1 mg/kg/dose ixabepilone). Treatment-related changes in serum chemistry were noted in males and females given the mid- and high-dose TFRP-1 (Groups 5 and 6, 1 and 2 mg/kg/dose ixabepilone) and the reference control IXEMPRA® (Group 3, 2 mg/kg/dose ixabepilone). Changes were similar between the 2 mg/kg/dose TFRP-1 and IXEMPRA® groups.

Increased alanine aminotransferase, aspartate aminotransferase, total bilirubin and total cholesterol were noted in males and/or females given 2 mg/kg/dose IXEMPRA® or 1 or 2 mg/kg/dose TFRP-1 on Day 32 relative to the saline control. The increases in these parameters correlated with the hepatic injuries observed in the histopathology of these animals.

All other differences observed in serum chemistry parameters, including those that were statistical significance, were considered incidental and unrelated to treatment because they were small in magnitude, not dose-related, and/or within the historical reference ranges of this laboratory.

Urinalysis

No treatment-related changes in urinalysis were noted in animals given the formulation control TFS-2 (Group 2) or the low- and mid-dose TFRP-1 (Groups 4 and 5, 0.1 and 1 mg/kg/dose ixabepilone). Decreased urine volume was noted on Day 32 in males and females given the high-dose TFRP-1 (Group 6, 2 mg/kg/dose ixabepilone) and the reference control IXEMPRA® (Group 3, 2 mg/kg/dose ixabepilone). Changes were similar between the 2 mg/kg/ dose TFRP-1 and IXEMPRA® groups. Decreased urine volume was still noted by the end of the recovery phase on Day 60 in females previously given 2 mg/kg/dose TFRP-1 and IXEMPRA®. These changes are summarized in Table 13 below. Noteworthy findings were characterized by their differences relative to the saline control animals.

TABLE 13

Treatment-Related Changes in Urinalysis (Percent Difference in Mean Values from Concurrent Controls)[a]

| | Doses (mg/kg/dose) | | | | | |
|---|---|---|---|---|---|---|
| | 0 | | 2 Test Article | | 2 | |
| | Saline | | Ixempra | | TFRP-1 | |
| | | | Sex | | | |
| | M | F | M | F | M | F |
| Day 32 - Dosing Phase (No. Animals) | 10 | 10 | 10 | 10 | 10 | 8 |
| Urine Volume (mL) | 16 | 10 | −66%** | −46%* | −23% | −37% |
| Day 60 - Recovery Phase (No. Animals) | 5 | 5 | 5 | 5 | 5 | 5 |
| Urine Volume (mL) | — | 12 | — | −60%** | — | −50%* |

[a]For controls, group means are shown. For treated groups, percent differences from controls are shown. Statistical significance is based on actual data (not on the percent differences).
Statistically significantly different from concurrent controls (saline): *p ≤ 0.05, **p ≤ 0.01.
A dash (—) indicates no test article treatment-related change in this group or not applicable.
M = Males, F = Females All other differences observed in urinalysis parameters, including those that were statistical significance, were considered incidental and unrelated to treatment because they were small in magnitude, not dose-related, and/or within the historical reference ranges of this laboratory.

Toxicokinetics

Blood samples from the control groups were collected and analyzed at 1 hour post-dose on Days 1 and 29, and the plasma concentrations of ixabepilone were all BLQ (<2.00 ng/mL). The data indicated that the control group was not exposed to the test article.

The $C_0$ and $AUC_{0-72\ h}$ values following once weekly IV injection of IXEMPRA® at 2 mg/kg/dose (Group 3) or TFRP-1 at 0.1, 1, or 2 mg/kg/dose of ixabepilone (Groups 4-6) to male and female rats for a total of 5 administrations are presented in Table 14.

There was no marked sex difference in systemic exposure ($AUC_{0-72\ h}$ and $C_0$) to ixabepilone at any dose level. As the dosage increased from 0.1 to 2 mg/kg, the systemic exposure ($AUC_{0-72\ h}$ and/or $C_0$) increased dose-proportionally in males on Day 29 but increased more than dose-proportionally in females on Day 1 and Day 29. There was no marked drug accumulation for ixabepilone at any dose level. After repeated IV injection of IXEMPRA® or TFRP-1 at 2 mg/kg of ixabepilone, the ratios of ixabepilone $AUC_{0-72\ h}$ (TFRP-1/IXEMPRA®) ranged from 0.99 to 1.2.

Pathology

Organ Weights—No treatment-related changes in terminal body weight or organ weights were noted in animals given the formulation control TFS-2 (Group 2) or the low-dose TFRP-1 (Group 4, 0.1 mg/kg/dose ixabepilone).

End of Dosing (Day 32)—Test article-related alterations were identified in the terminal body weight and organ weights (thymus, prostate gland, ovaries, uterus with cervix and testes) at the end of dosing.

Terminal Body Weight—Dose-dependent decreased mean terminal body weights compared to Group 1 (saline) control animals were identified for Group 5 (1 mg/kg/dose TFRP-1) and Group 6 (2 mg/kg/dose TFRP-1) animals.

Thymus—Decreased mean thymus weight in Group 6 (2 mg/kg/dose TFRP-1) compared to Group 1 (saline) control animals correlated microscopically with minimal to severe decreased lymphocyte cellularity in the thymic cortex of the affected group.

Liver—Increased mean liver weight in Group 6 (2 mg/kg/dose TFRP-1) females was without a correlating microscopic finding.

Prostate Gland—Decreased mean prostate gland weight in Group 6 (2 mg/kg/dose TFRP-1) compared to Group 1 (saline) control males correlated microscopically with mild prostate gland atrophy.

Ovaries and Uterus—Decreased mean ovaries and uterus weights in Group 6 (2 mg/kg/dose TFRP-1) compared to Group 1 (saline) control females correlated microscopically with the presence of decreased number/absent corpora lutea and increased number of atretic follicles in the ovaries, and mild uterine (uterus with cervix) atrophy in the affected group.

TABLE 14

The $C_0$ and $AUC_{0-72\ h}$ Values Following Once Weekly IV Injection.

| Group | Dose (mg/kg) | Study Day | Sex | $C_0$ (ng/mL) | $AUC_{0-72\ h}$ (h*ng/mL) |
|---|---|---|---|---|---|
| Group 3-Ixempra | 2 | 1 | Male | 1970 | 1080 |
| | | | Female | 1970 | 1390 |
| | | 29 | Male | 3020 | 1410 |
| | | | Female | 1850 | 1260 |
| Group 4-TFRP-1 | 0.1 | 1 | Male | 37.3 | NA |
| | | | Female | 32.4 | 24.1 |
| | | 29 | Male | 102 | 51.1 |
| | | | Female | 71.5 | 34.4 |
| Group 5-TFRP-1 | 1 | 1 | Male | 507 | 455 |
| | | | Female | 458 | 492 |
| | | 29 | Male | 1260 | 835 |
| | | | Female | 907 | 672 |
| Group 6-TFRP-1 | 2 | 1 | Male | 2330 | 1120 |
| | | | Female | 2200 | 1380 |
| | | 29 | Male | 3160 | 1440 |
| | | | Female | 2720 | 1450 |

NA: Not applicable due to insufficient quantifiable time points.

Testes—Decreased mean absolute and relative to brain testes weight were identified for Group 6 (2 mg/kg/dose TFRP-1) compared to Group 1 (saline) control males, which correlated microscopically with mild germ cell degeneration/depletion in the affected group. The weight of the testes typically does not vary with body weight, so the lack of concordance in the direction of the absolute and relative (/body weight) changes in testes weight was discounted in this assessment.

The mean terminal body weights and organ weights for the Group 6 (2 mg/kg/dose TFRP-1) animals were not substantially different from the Group 3 (2 mg/kg/dose IXEMPRA®) animals.

Testes—Decreased mean testes weight in Group 6 (2 mg/kg/dose TFRP-1) compared to Group 1 (saline) control males was without a microscopic correlate.

The mean terminal body weights and organ weights for the Group 6 (2 mg/kg/dose TFRP-1) animals were not substantially different from the Group 3 (2 mg/kg/dose IXEMPRA®) animals. However, a correlating microscopic finding for the mean testes weight decrease of mild degeneration/atrophy of seminiferous tubules was identified in two Group 3 (2 mg/kg/dose IXEMPRA®) animals, but not in Group 6 (2 mg/kg/dose TFRP-1) animals.

TABLE 15

Terminal Selected Organ Weight Alterations on Day 32

| Sex: | | Male | | | | Female | | | |
|---|---|---|---|---|---|---|---|---|---|
| Group: | | 3 | 4 | 5 | 6 | 3 | 4 | 5 | 6 |
| Ixabepilone (mg/kg/dose): | | 2 | 0.1 | 1 | 2 | 2 | 0.1 | 1 | 2 |
| TFS-2 (mg/kg/dose) | | 0 | 0.5 | 5.0 | 10.0 | 0 | 0.5 | 5.0 | 10.0 |
| TFRP-1 (mg/kg/dose) | | 0 | 1.1 | 11.1 | 22.2 | 0 | 1.1 | 11.1 | 22.2 |
| Number of animals: | | 10 | 10 | 10 | 10 | 10 | 10 | 10 | 8 |
| Terminal Body Weight | | −22% | — | *−10%* | *−22%* | −22% | — | *−14%* | *−24%* |
| Thymus | absolute | −77% | — | — | *−67%* | −81% | — | — | *−85%* |
| | /body weight | −71% | — | — | *−58%* | −77% | — | — | *−81%* |
| | /brain weight | −76% | — | — | *−65%* | −80% | — | — | *−85%* |
| Liver | absolute | — | — | — | — | +6% | — | — | +3% |
| | /body weight | — | — | — | — | +35% | — | — | +37% |
| | /brain weight | — | — | — | — | +11% | — | — | +6% |
| Testes | absolute | −11% | — | — | *−9%* | — | — | — | — |
| | /body weight | +12% | — | — | *+15%* | — | — | — | — |
| | /brain weight | −8% | — | — | *−4%* | — | — | — | — |
| Prostate | absolute | −29% | — | — | *−42%* | — | — | — | — |
| gland | /body weight | −10% | — | — | *−25%* | — | — | — | — |
| | /brain weight | −27% | — | — | *−38%* | — | — | — | — |
| Ovaries | absolute | — | — | — | — | −39% | — | — | *−40%* |
| | /body weight | — | — | — | — | −23% | — | — | *−22%* |
| | /brain weight | — | — | — | — | −35% | — | — | *−38%* |
| Uterus, with | absolute | — | — | — | — | −57% | — | — | *−58%* |
| cervix | /body weight | — | — | — | — | −46% | — | — | *−46%* |
| | /brain weight | — | — | — | — | −55% | — | — | *−58%* |

Numbers represent the percent difference compared to Group 1 (saline) control animals, rounded to the nearest whole number. Changes in boldface type were statistically different from the Group 1 (saline) control animals. Weights for animals in Groups 4-6 were also compared statistically to those for animals in Group 2 (TFS controls). Statistically significant differences from Group 2 are shown in italics.
"—" not applicable.

End of Recovery (Day 60)—Test article-related alterations were identified in the terminal body weight and organ weights (testes and epididymides) at the end of the recovery period. All other organ weight alterations identified at the end of dosing had reversed completely by the end of the recovery period.

Terminal Body Weight—Decreased mean terminal body weight was still evident for Group 6 (2 mg/kg/dose TFRP-1) animals at the end of the recovery period, although the difference from Group 1 (saline) control animals was of lesser magnitude, especially for the females, than at the end of dosing.

Epididymides—Decreased mean epididymides weight in Group 6 (2 mg/kg/dose TFRP-1) compared to Group 1 (saline) control males correlated microscopically with mild or moderate decreased sperm/increased cell debris in the epididymal lumen.

TABLE 16

Selected Organ Weight Alterations on Day 60

| Sex: | | Male | | Female | |
|---|---|---|---|---|---|
| Group: | | 3 | 6 | 3 | 6 |
| Ixabepilone (mg/kg/dose): | | 2 | 2 | 2 | 2 |
| TFS-2 (mg/kg/dose) | | 0 | 10.0 | 0 | 10.0 |
| TFRP-1 (mg/kg/dose) | | 0 | 22.2 | 0 | 22.2 |
| Number of animals: | | 5 | 5 | 5 | 5 |
| Terminal Body Weight | | −20% | *−18%* | −5% | *−9%* |
| Epididymides | absolute | −39% | *−39%* | — | — |
| | /body weight | −24% | *−26%* | — | — |
| | /brain weight | −34% | *−35%* | — | — |
| Testes | absolute | −23% | *−15%* | — | — |
| | /body weight | −4% | +3% | — | — |
| | /brain weight | −17% | −8% | — | — |

Numbers represent the percent difference compared to Group 1 (saline) control animals, rounded to the nearest whole number. Changes in boldface type were statistically different from the Group 1 (saline) control animals. Weights for animals in Group 6 were also compared statistically to those for animals in Group 2 (TFS controls). Statistically significant differences from Group 2 are shown in italics.
"—" = not applicable.

All other differences among groups in organ weight parameters at the end of dosing and the end of the recovery period, regardless of statistical significance, were unrelated to administration of the test article because they were secondary to decreased body weight, were of negligible magnitude, were without a dose response to the test article, lacked concordance in the direction/magnitude of change between absolute and relative organ weight changes, and/or were within the range of expected variation for the species.

Necropsy

End of Dosing (Day 32)

Liver—Test article-related macroscopic observations were identified in the liver of one Group 6 (2 mg/kg/dose TFRP-1) female. Multifocal dark discoloration in liver (more than 10 foci, pinpoint, all lobes) of Group 6 female 6507 correlated microscopically with multifocal moderate coagulative necrosis in the liver. All other macroscopic observations at the end of dosing were related to the injection procedure or were consistent with spontaneous background findings or euthanasia artifact.

End of Recovery (Day 60)

There were no macroscopic observations on Day 60.

Histopathology (Microscopic Observations)

No treatment-related microscopic findings were noted in animals given the formulation control TFS-2 (Group 2) or the low-dose TFRP-1 (Group 4, 0.1 mg/kg/dose ixabepilone).

End of Dosing (Day 32)

Test article-related microscopic findings were identified in the sciatic nerves, liver, stomach, small intestines (duodenum, jejunum and ileum), large intestines (cecum, colon and rectum), mandibular salivary glands, pancreas, sternal bone marrow, thymus, spleen, mandibular lymph node, mesenteric lymph node, testes, epididymides, prostate gland, seminal vesicles, ovaries, uterus (including cervix), vagina, fallopian tubes, inguinal mammary glands (females only), femoral bone (including stifle joint) and Harderian glands. Findings in the sciatic nerves, gastrointestinal system, male and female reproductive systems and Harderian gland were adverse in Group 5 (1 mg/kg/dose TFRP-1) and Group 6 (2 mg/kg/dose TFRP-1) animals. Additional adverse findings were identified in the liver, hematopoietic system, lymphoid system, and femur of Group 6 animals.

Nervous System: Dose-dependent, minimal or mild multifocal (±unilateral) degeneration of sciatic nerve axons were identified in Group 5 (1 mg/kg/dose TFRP-1) and Group 6 (2 mg/kg/dose TFRP-1) animals. Axon degeneration was considered adverse in Group 5 and Group 6 animals.

Liver: Minimal hepatocyte single-cell necrosis/apoptosis and minimal increased hepatocyte mitotic figures were identified in Group 6 (2 mg/kg/dose TFRP-1) females. Minimal to moderate, multifocal coagulative necrosis of hepatocytes was identified in Group 6 (2 mg/kg/dose TFRP-1) males and females, although females were affected to a greater extent than males. In one Group 6 female, this finding correlated with macroscopic multifocal dark discoloration in the liver. Coagulative necrosis and/or single-cell necrosis/apoptosis in Group 6 animals correlated with increased alanine aminotransferase and aspartate aminotransferase activities. Single-cell necrosis/apoptosis and coagulative necrosis were considered adverse in Group 6 animals. Extramedullary hematopoiesis is discussed below with the hematopoietic system.

Gastrointestinal system: Minimal or mild single-cell necrosis/apoptosis of the glandular mucosa of the stomach was identified in Group 6 (2 mg/kg/dose TFRP-1) females and was sometimes accompanied by mild mucosal atrophy secondary to the loss of mucosal epithelium. Minimal or mild single-cell necrosis/apoptosis of the mucosa of the duodenum, jejunum and/or ileum was identified in Group 5 (1 mg/kg/dose TFRP-1) and Group 6 (2 mg/kg/dose TFRP-1) animals. Single-cell necrosis/apoptosis was variably accompanied by the secondary change of minimal to moderate villus atrophy, which resulted from the loss of mucosal epithelium. Minimal to moderate reactive mucosal hyperplasia in the small intestines of Group 5 and Group 6 animals was a reparative response. Minimal single-cell necrosis/apoptosis and minimal increased mitotic figures were also identified in Brunner's glands (duodenum) of Group 6 females. Minimal to moderate single-cell necrosis/apoptosis in the mucosa of the cecum, colon and rectum was identified in Group 5 (1 mg/kg/dose TFRP-1) and Group 6 (2 mg/kg/dose TFRP-1) animals. Minimal to moderate reactive mucosal hyperplasia in the large intestines of Group 5 and Group 6 animals was a reparative response. Single-cell necrosis/apoptosis and reactive hyperplasia occurred in a dose-dependent manner in the cecum and rectum. In the cecum, the single-cell necrosis/apoptosis in Group 6 animals was accompanied by minimal to moderate neutrophilic inflammation in the mucosa, which was considered secondary to loss of the mucosal barrier function. Minimal single-cell necrosis/apoptosis of mandibular salivary gland acinar cells were identified in Group 6 (2 mg/kg/dose TFRP-1) females. Minimal or mild salivary gland acinar cell hypertrophy in Group 6 animals may have been a compensatory response to loss of acinar cells. Dose-dependent single-cell necrosis/apoptosis and increased mitotic figures in pancreatic acinar cells were identified in Group 5 (1 mg/kg/dose TFRP-1) and Group 6 (2 mg/kg/dose TFRP-1) animals. Minimal to moderate increased incidence and severity of peri-insular halos was also identified in Group 6 animals, which may have been a compensatory response. Females were affected to a greater extent than males. Single-cell necrosis/apoptosis in multiple gastrointestinal organs of Group 5 and Group 6 animals was considered adverse.

Hematopoietic System: Dose-dependent minimal to marked decreased hematopoietic cellularity was identified in the sternal bone marrow of animals in Group 5 (1 mg/kg/dose TFRP-1) and Group 6 (2 mg/kg/dose TFRP-1), which correlated with decreased circulating red blood cell mass and decreased reticulocytes in Group 5 and Group 6 animals. Minimal or mild increased hematopoiesis in the spleen of Group 6 animals and minimal dose-dependent extramedullary hematopoiesis in the liver of Group 5 and Group 6 animals were considered a regenerative response to the hematopoietic losses in the bone marrow. Decreased hematopoietic cellularity in the bone marrow was considered adverse at the magnitude observed in Group 6 animals.

Lymphoid System: Minimal to severe decreased lymphocyte cellularity was identified in the thymic cortex, spleen and mandibular and mesenteric lymph nodes in Group 6 (2 mg/kg/dose TFRP-1) animals. Decreased lymphocyte cellularity in the thymus correlated with decreased mean thymus weight for the affected group and was often accompanied by minimal to moderate increased lymphocyte apoptosis. Decreased lymphocyte cellularity in the thymus and lymph nodes affected females to a greater extent than males. Minimal or mild decreased lymphocyte cellularity was also identified in the gastrointestinal-associated lymphoid tissue (GALT, jejunum and/or ileum) of Group 6 females. Decreased lymphocyte cellularity in the lymphoid system of Group 6 animals was considered adverse. Minimal decreased lymphocyte cellularity in the thymic cortex of one Group 2 female was considered spontaneous.

Male Reproductive System: Mild germ cell degeneration/depletion in the testes of Group 6 (2 mg/kg/dose TFRP-1) animals correlated with decreased mean absolute and relative (/brain) testes weight, and was accompanied by the related finding of minimal to moderate decreased sperm/increased cell debris in the epididymal lumen. Minimal or mild single-cell necrosis/apoptosis in the epididymal epithelium in Group 6 animals was accompanied by minimal or mild reactive hyperplasia as a reparative response. Minimal or mild single-cell necrosis/apoptosis of the prostatic epithelium in Group 6 animals was accompanied by mild prostate gland atrophy, correlated with decreased mean prostate gland weight. Minimal or mild single-cell necrosis/apoptosis of the seminal vesicle epithelium in Group 5 (1 mg/kg/dose TFRP-1) and Group 6 (2 mg/kg/dose TFRP-1) animals was accompanied by dose-dependent minimal to moderate reactive hyperplasia as a reparative response. Germ cell degeneration/depletion and single-cell necrosis/apoptosis in reproductive organs of Group 5 and Group 6 animals were considered adverse.

Female Reproductive System: Increased incidence of animals with luteal cysts and minimal or mild hemorrhage in corpora lutea were identified in females in Group 5 (1 mg/kg/dose TFRP-1) and Group 6 (2 mg/kg/dose TFRP-1). Two animals in Group 6 also had increased number of atretic follicles and decreased number/absent corpora lutea, which correlated with decreased mean ovaries weight. Ovarian findings in Group 6 females were often accompanied by mild atrophy of the uterus, with decreased mean uterus weight, and mild atrophy and increased mucification of the vaginal epithelium. These findings indicate test article-related alterations in the female reproductive cycle. Minimal increased mitotic figures in the fallopian tube epithelium and minimal single-cell necrosis/apoptosis of the ductular/alveolar epithelium of the mammary glands were also identified in Group 6 females. Microscopic findings in the ovaries, uterus and vagina that were consistent with altered reproductive cycling in Group 5 and Group 6 animals and mammary gland single-cell necrosis/apoptosis in Group 6 animals were considered adverse.

Other: Minimal or mild decreased trabecular bone in the femur (bone, femur, including stifle joint) was identified in Group 6 (2 mg/kg/dose TFRP-1) animals. Females were affected to a greater extent than males. Dose-dependent minimal or mild Harderian gland acinar cell single-cell necrosis/apoptosis was identified in Group 5 (1 mg/kg/dose TFRP-1) and Group 6 (2 mg/kg/dose TFRP-1) animals. In the Group 6 females, the single cell necrosis/apoptosis was accompanied by reactive hyperplasia of acinar cells as a reparative response. Single-cell necrosis/apoptosis of Harderian gland acinar cells in Group 5 and Group 6 animals and decreased trabecular bone in the femur of Group 6 animals were considered adverse. All microscopic findings and correlating organ weight alterations identified for Group 6 (2 mg/kg/dose TFRP-1) animals at the end of dosing were similar in incidence and severity to those in Group 3 (2 mg/kg/dose IXEMPRA®) animals.

End of Recovery (Day 60)

Test article-related microscopic findings were still present in the sciatic nerves, sternal bone marrow, epididymides, ovaries, vagina, and Harderian glands at the end of recovery, although at reduced magnitude and severity compared to the end of dosing, indicating partial reversibility. These are summarized in Text Table 15.9.3-2. All other findings identified at the end of dosing reversed completely by the end of the recovery period. Minimal sciatic nerve axon degeneration was still present in some Group 6 (2 mg/kg/dose TFRP-1) animals, although at a reduced incidence and severity compared to the end of dosing. Mild decreased hematopoietic cellularity was still present in the sternal bone marrow of one Group 6 (2 mg/kg/dose TFRP-1) animal, although at a reduced incidence and severity compared to the end of dosing.

Microscopic findings in the testes of Group 6 (2 mg/kg/dose TFRP-1) animals reversed completely by the end of the recovery period, although the mean testes weight was still slightly decreased. Mild or moderate decreased sperm/increased cell debris was still present in the lumen of the epididymides of Group 6 males, with correlating decreased mean epididymides weight. The persistence of the decreased sperm/increased cell debris in the epididymides was attributed to the expected lag between recovery of spermatogenesis in the testes and reconstitution of sperm stores in the epididymides. Minimal reactive hyperplasia was still present in the epididymal epithelium, although the finding was reduced in magnitude compared to the end of dosing. Minimal degeneration/atrophy and minimal decreased sperm/increased cell debris in the testes of a Group 1 (saline) control animal was considered spontaneous. Luteal cysts were still present in the ovaries of two females and were accompanied by decreased number/absent corpora lutea and follicular cysts in one animal and minimal hemorrhage in corpora lutea in the second animal.

While these findings indicate ongoing alterations in the reproductive cycle, fewer animals were affected than at the end of dosing, which indicates partial reversibility of reproductive cyclicity during the recovery period. Minimal reactive hyperplasia was still present in the Harderian glands of one Group 6 (2 mg/kg/dose TFRP-1) animal, although the incidence and severity of this finding were reduced compared to the end of dosing. Microscopic findings and correlating organ weight alterations identified for Group 6 (2 mg/kg/dose TFRP-1) animals at the end of the recovery period were similar in incidence and severity to those in Group 3 (2 mg/kg/dose IXEMPRA®) animals. Mild degeneration/atrophy of seminiferous tubules in the testes of Group 3 males at the recovery sacrifice correlated with decreased mean testes weight and was a sequela of progression of the germ cell degeneration/depletion identified at the end of dosing and/or delayed recovery of spermatogenesis. The difference between the degree of reversal of findings in the Group 6 testes compared to Group 3 testes was not considered meaningful.

All other microscopic findings at the end of dosing and the end of the recovery period were unrelated to the test article administration because they occurred only sporadically and without evidence of dose response to the test article, they were of low incidence and severity and/or they were observed with comparable incidence and severity in vehicle control animals, and/or they were considered common incidental findings in rats.

Determination of Ixabepilone in Rat Plasma

Plasma samples were taken from the rats on study day 1 and 29 indicated that administration of TFRP-1 resulted in acceptable plasma concentration levels of ixabepilone for clinical efficacy. The collection schedule for the rat plasma samples is presented in Table 17.

TABLE 17

Collection Schedule for Rat Plasma Samples

| Dose Groups | Approximate Time Point (postdose) | Treatment Groups (6 rats/sex/group) Groups 3, 4, 5 and 6 | Control Group (3 rats/sex) Groups 1 and 2 |
|---|---|---|---|
| 1st 3 of 6 animals | Predose | X | — |
| 2nd 3 of 6 animals | 1 min (0.017 h) | X | — |
| 1st 3 of 6 animals | 1 h | X | X (all three animals) |
| 2nd 3 of 6 animals | 3 h | X | — |
| 1st 3 of 6 animals | 6 h | X | — |
| 2nd 3 of 6 animals | 9 h | X | — |
| 1st 3 of 6 animals | 18 h | X | — |
| 2nd 3 of 6 animals | 24 h | X | — |
| 1st 3 of 6 animals | 72 h | X | — |

X—Blood sample collection on Day 1 and Day 29 of the study;
—: Not applicable.
Note:
If TK animal death occurs, Study Director may reassign animals for scheduled blood collection.

Conclusion

In conclusion, the test article TFRP-1 in dosages of 0.1, 1 and 2 mg/kg/dose of ixabepilone, the saline control, the formulation control TFS-2 (10 mg/kg/dose), the reference control IXEMPRA® (2 mg/kg/dose ixabepilone) were administered in five weekly doses by intravenous injection to Sprague-Dawley rats followed by a 28-day recovery period. TFRP-1 administration resulted in two unscheduled deaths at 2 mg/kg/dose and adverse changes at >1 mg/kg/dose. Administration of the formulation control TFS-2 alone did not result in any toxic effects. TFRP-1 and IXEMPRA® administration at the same dose level (2 mg/kg/dose) of ixabepilone resulted in comparable systemic exposures and similar toxic effects. Consequently, the No Observed Adverse Effect Level (NOAEL) and the Severely Toxic Dose in 10% of the animals (STD 10) were considered to be 0.1 mg/kg/dose of ixabepilone (equivalent to 1.1 mg/kg/dose TFRP-1) and 2 mg/kg/dose of ixabepilone (equivalent to 22.2 mg/kg/dose TFRP-1), respectively, under the conditions of the study. The corresponding $AUC_{0-72\,h}$ and $C_0$ of ixabepilone following the last dose of TFRP-1 at the NOAEL were 51.1 h*ng/mL and 102 ng/mL for males and 34.4 h*ng/mL and 71.5 ng/mL for females, respectively. The corresponding $AUC_{0-72\,h}$ and $C_0$ of ixabepilone following the last dose of TFRP-1 at the STD 10 were 1440 h*ng/mL and 3160 ng/mL for males and 1450 h*ng/mL and 2720 ng/mL for females, respectively.

Example 9. Quantitative Whole-Body Autoradiography Study in Rats

This non-GLP study was designed to assess adsorption, distribution, metabolism and elimination of polymer excipient TFS-2 in albino and pigmented rats using quantitative whole-body autoradiography (QWBA). TFS-2 was labelled with $^{14}C$ acetic anhydride according to the following synthetic scheme:

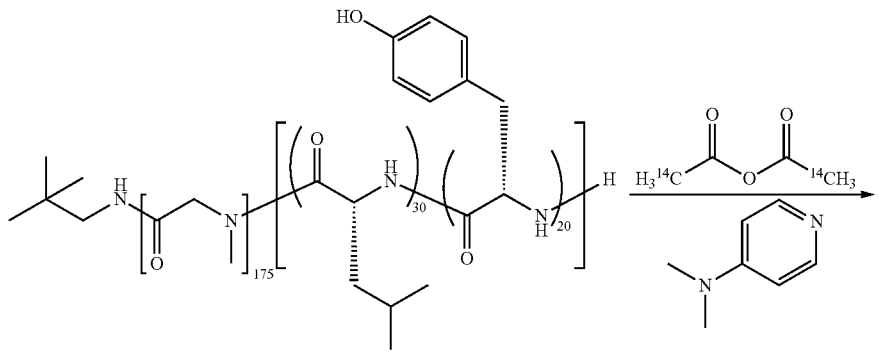

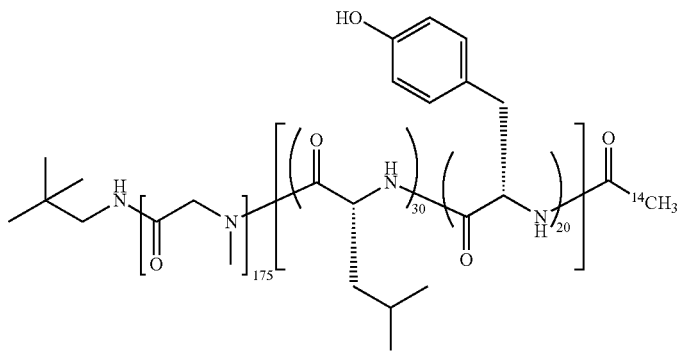

The rats in the study were divided into three groups as presented in the experimental design in Table 18. Each rat in Groups 1, 2, and 3 received a nominal single IV dose of [$^{14}$C]-TFS-2 at 50 mg/kg and a radioactivity dose of 100 µCi/kg. Group 1 (n=12) was used for the TD portion of this study for male LE rats. Group 2 (n=16) was used for the TD portion of this study for male SD rats. Group 3 (n=16) was used for the TD portion of this study for female SD rats. The dosing vehicle was 0.9% saline for injection.

and blood (approximately 5 mL) was collected by cardiac puncture into a syringe containing K2EDTA (anticoagulant). The animals were sacrificed by an inhalation overdose of isoflurane. Blood samples were thoroughly mixed by gently inverting the tube and placing on wet ice (or equivalent) immediately after collection.

Approximately 0.5 mL of the whole blood sample was stored at approximately −70° C. for possible reanalysis. Two aliquots of the whole blood sample, each approximately

TABLE 18

Experimental Design for QWBA Study

| Group | Route of Admin | Study Design | # Animals/ Gender - Type | Dose Level (tentative) mg/kg (mg/kg/h) | µCi/kg (µCi/kg/h) | mL/kg (mL/kg/h) | Collection Matrices and Time Points/Intervals Post-Dose |
|---|---|---|---|---|---|---|---|
| 1 | IV (bolus)$^a$ | Tissue Distribution$^b$ | 12 M LE | 50 | 100 | 10 | Blood/Plasma and Carcass for QWBA: 1, 6, 24, 72, 168, and 336 h from the start of infusion |
| 2 | IV (bolus)$^a$ | Tissue Distribution$^b$ | 16 M SD | 50 | 100 | 10 | Blood/Plasma and Carcass for QWBA: 0.5, 1, 3, 6, 24, 72, 168, and 336 h from the start of infusion |
| 3 | IV (bolus)$^a$ | Tissue Distribution$^b$ | 16 F SD | 50 | 100 | 10 | Blood/Plasma and Carcass for QWBA: 0.5, 1, 3, 6, 24, 72, 168, and 336 h from the start of infusion |

$^a$Slow push 1 minute intravenous administration via the tail vein.
$^b$Two animals per time point per sex, terminal bleeds by cardiac puncture under isoflurane-induced anesthesia, plasma separated by chilled centrifugation
LE: Long-Evans, SD: Sprague Dawley; IV: Intravenous Preparation of the Dosing Formulation The target concentrations of the IV dose formulation was 5 mg/mL in order to deliver the target dose of 50 mg/kg (100 µCi/kg) when administered at the target dose volume of 10 mL/kg.

A 400-mL, autoclaved/sterilized glass vial was designated as the formulation vessel, a stir bar added and the vessel weighed. First, the [$^{14}$C]-TFS-2 stock material was dissolved in 15 mL sterile saline, added directly into the container it was received in. The volume of the stock material needed was then determined (3300 µCi/(2.63 µCi/mg)=1.254 g [2700 Xi]=1.254 mL) and transferred into the formulation vessel. Next, a 0.4137 g aliquot of TFS-2 (0.4137 g×0.957 [purity]=0.396 g) was weighed and added to the formulation vessel. The solution was then diluted to 300 mL with sterile saline allowed to stir for approximately 45 minutes (min) until a solution was achieved. The final, appearance of the formulation was observed to be a slightly hazy colorless solution with a pH of 7.0. The formulation was continuously stirred during analysis.

Dose Administration

Each animal was weighed on the day of dose administration. The dose formulation stirred continuously throughout dose administration. [$^{14}$C]-TFS-2 dose solution at 10 mL/kg, 50 mg/kg target dose, was administered to the rats via tail vein using a 3-mL syringe with a 25-gauge beveled needle attached. Each dosing syringe was weighed before and after dosing, and the emptied syringe weight was subtracted from the loaded syringe weight to determine the actual dose amount of formulation delivered to each rat. The dose calculation was based on the actual weight delivered, multiplied by the test article concentration determined from the dose analysis.

Sample Collection

At the designated time points, one animal per time point from Groups 1, 2, and 3 were anesthetized with isoflurane 0.100 mL, were pipetted and weighed into combustion vessels for combustion and radiometric analysis. The remaining blood sample was centrifuged at approximately 4° C. for 10 minutes at 2500 rpm to isolate plasma.

Two aliquots of the plasma were pipetted and weighed into scintillation vials and vortexed prior to radiometric analysis. The remaining plasma sample was stored at approximately −70° C. for possible reanalysis and future use.

All animals were euthanized by an inhalation overdose of isoflurane. All animals were frozen in a specified standard conformation by submerging the carcass in a dry ice/hexane bath, and then storing it at approximately −20° C. until processed by QWBA techniques. The QWBA preparation is as follows. The legs and tail were removed from each carcass. Any residual hexane was quickly rinsed off using cold tap water and soap. The frozen carcasses were then individually set in a molding frame/stage assembly, submerged in 5% (by volume) low viscosity carboxymethylcellulose (CMC), and placed in a dry ice/hexane bath. Once the blocked carcasses (sample blocks) were frozen, they were removed from the dry ice/hexane bath and placed in storage (approximately −20° C.) for at least 12 h prior to sectioning.

QWBA Processing

Sagittal, 30-µm thick sections of the CMC-embedded rat carcasses, including QC standards, and the CMC-embedded calibration standards, were sectioned using a Leica 9800 Cryomicrotome (Leica Biosystems, St. Louis, Mo.) with the temperature maintained at approximately −20° C. The sections were transferred using no. 821 SCOTCH® brand tape (3M, St. Paul, Minn.). Two sections for each anatomical area of interest, containing one or more tissues of interest, were collected in close proximity to each other. The sections were dehydrated for at least 48 h in the cryomicrotome chamber (approximately −20° C.) and then transferred to a desiccant storage box for at least 1 h. The sections were removed from their frames, mounted on a support cardboard backing, labeled with radioactive ink, and then wrapped in plastic wrap.

The phosphor imaging plates (IP), BAS-SR 2025 (Fujifilm, Tokyo, Japan), were exposed to uniformly bright visible light for at least 40 min using an IP eraser (Fujifilm, Tokyo, Japan) to remove any residual latent images. Whole body sections, containing their QC standards, were placed in IP cassettes along with a section containing blood calibration standards. The wrapped sections were placed in direct contact with an IP. The IPs were exposed to the sections for approximately 4 days while stored at room temperature in a copper-lined lead shielded box to minimize background radiation. Autoradioluminograms were generated in a darkroom with the lights off using a GE Typhoon FLA 9500 Phosphor Imager (GE, Pittsburgh, Pa.) and analyzed using AIDA software (Raytest GmbH, Berlin, Germany). The radioactivity concentrations in selected tissues were determined by digital analysis of the photo-stimulated light/unit area ($PSL/mm^2$) on each autoradioluminogram. A calibration curve was established for each IP using AIDA software, the $PSL/mm^2$ response (y) and the radioactive concentration of the calibration standards (x) were fit with least-squares regression analysis to the linear function with $1/x^2$ weighting. Concentrations of radioactivity were back-calculated from the results of the regression analysis using the AIDA software.

Tissues and Area of Interest (AOI)

Selected tissues (nomenclature used for both organs and tissues) and areas of interest (AOI) were analyzed the QWBA techniques. The tissues and AOI were analyzed within Advanced Image Data Analysis (AIDA) software (Raytest GmbH, Berlin, Germany) using a region sampling tool. All tissues and AOI per carcass were analyzed and a single value for the concentration of the derived radioactivity was reported. The following tissues and AOI were analyzed for all study animals:

Adrenal gland
Adrenal cortex
Adrenal medulla
Aorta
Bile (in duct)
Blood (cardiac)
Bone (femur)
Bone marrow (femur)
Brain (whole)
Brown fat
Cecum contents
Cecum mucosa
Epididymis (male only)
Esophagus wall
Ex-orbital lachrymal gland
Eye
Harderian gland
Heart
Intra-orbital lachrymal gland
Kidney
Kidney cortex
Kidney medulla
Large intestine contents
Large intestine wall
Lens
Liver
Lung
Lymph node (cervical)
Mammary gland region (female only)
Muscle (femoral)
Nasal turbinates
Non-pigmented skin
Oral mucosa
Ovary (female only)
Pancreas
Pigmented skin (LE only)
Pituitary gland
Prostate (male only)
Salivary gland
Seminal vesicle (male only)
Small intestine contents
Small intestine wall
Spinal cord
Spleen
Stomach contents
Stomach wall (glandular)
Stomach wall (non-glandular)
Testis (male only)
Thymus
Thyroid gland
Trachea
Urinary bladder contents
Urinary bladder wall
Uterus (female only)
Uveal tract
Vagina (female only)
White fat (inguinal)

The target dose was 50 mg/kg and 100 μCi/kg for the dosing formulation. The mean dose mg/kg and mean μCi/kg for Groups 1 through 3 are listed below.

TABLE 19

Mean Dose and Mean Radioactive Dose for Groups 1-3

| Group Number | Mean Dose (mg/kg) | Mean Radioactive Dose (μCi/kg) |
|---|---|---|
| Group 1 Male Long-Evans - Intact (QWBA) | 49.2 | 98.3 |
| Group 2 Male Sprague Dawley - Intact (QWBA) | 48.8 | 97.5 |
| Group 3 Female Sprague Dawley - Intact (QWBA) | 49.1 | 98.1 |

The Test Article was well-tolerated. The rats appeared to be normal throughout the study and demonstrated no significant adverse effects from the drug administration.

Distribution of Radioactivity in Male Long-Evans Rats (Group 1)

For the TD group (Group 1 LE males), $C_{max}$ values of 385 µg equiv/g and 216 µg equiv/g were obtained in plasma and blood, respectively, at 1 h post-dose (the first sampling time point), following a single IV dose of 50 mg/kg (100 µCi/kg) [$^{14}$C]-TFS-2 to male LE rats. The total plasma radioactivity decreased steadily after $t_{max}$ and was not BQL at 336 h post-dose. Blood concentrations were slightly lower than plasma concentrations for all time points post-dose and did not reach BQL levels at 336 h post-dose. The majority of tissues had $t_{max}$ values at 1 h post-dose, but all tissues were not BQL by 336 h post-dose, except for the brain (whole) and lens. The majority of tissues had tissue:plasma $AUC_{0-t}$ ratios less than 1.

The [$^{14}$C]-TFS-2-derived radioactivity $C_{max}$ in tissues other than blood ranged from 708 µg equiv/g in the urinary bladder wall to 0.468 µg equiv/g in the lens following an IV (50 mg/kg) dose of [$^{14}$C]-TFS-2 to male LE rats. The majority of peak tissue radioactivity concentrations were observed at 1 h after dosing, except for aorta, epididymis, spinal cord, and trachea, which occurred at 6 h; ex-orbital lachrymal gland, Harderian gland, meninges, pancreas, thymus, and thyroid gland, which occurred at 24 h; bone marrow (femur), large intestine wall, liver, non-pigmented skin, and white fat (inguinal), which occurred at 72 h; cecum mucosa, nasal turbinates, spleen, and stomach wall (non-glandular), which occurred at 168 h; and lymph node (cervical), which occurred at 336 h after dosing.

Distribution of Radioactivity in Male Sprague Dawley Rats (Group 2)

For the TD group (Group 2 SD males), $C_{max}$ values of 390 µg equiv/g and 237 µg equiv/g were obtained in plasma and blood, respectively, at 0.5 h post-dose (the first sampling time point), following a single IV dose of 50 mg/kg (100 µCi/kg) [$^{14}$C]-TFS-2 to male SD rats. The total plasma radioactivity decreased steadily after $t_{max}$ and was not BQL at 336 h post-dose. Blood concentrations were lower than plasma concentrations for all time points post-dose and did not reach BQL levels at 336 h post-dose. The majority of tissues had $t_{max}$ values at 0.5 h post-dose, but all tissues were not BQL by 336 h post-dose, except for the brain (whole); the lens did not have observed concentrations above the LLOQ at any time points post-dose. The majority of tissues had tissue:plasma $AUC_{0-t}$ ratios less than 1.

The [$^{14}$C]-TFS-2-derived radioactivity $C_{max}$ in tissues other than blood ranged from 380 µg equiv/g in the urinary bladder wall to 3.33 µg equiv/g in the brain (whole) following a IV (50 mg/kg) dose of [$^{14}$C]-TFS-2 to male SD rats. The majority of peak tissue radioactivity concentrations were observed at 0.5 h after dosing, except for eye, meninges, muscle (femoral), non-pigmented skin, prostate, small intestine wall, urinary bladder wall, and all sub-structures of the adrenal gland, which occurred at 1 h; aorta, brown fat, liver, spinal cord, and testis, which occurred at 3 h; seminal vesicle and trachea, which occurred at 6 h; cecum mucosa, Harderian gland, large intestine wall, and white fat (inguinal), which occurred at 24 h; bone (femur) and thyroid gland, which occurred at 72 h; stomach wall (non-glandular) and uveal tract, which occurred at 168 h; and bone marrow (femur), lymph node (cervical), and spleen, which occurred at 336 h after dosing. The lens did not have observed concentrations above the LLOQ (<0.269 µg equiv/g) at any time points post-dose.

Distribution of Radioactivity in Female Sprague Dawley Rats (Group 3)

For the TD group (Group 3 SD females), $C_{max}$ values of 419 µg equiv/g and 246 µg equiv/g were obtained in plasma and blood, respectively, at 0.5 h post-dose (the first sampling time point), following a single IV dose of 50 mg/kg (100 µCi/kg) [$^{14}$C]-TFS-2 to female SD rats. The total plasma radioactivity decreased steadily after $t_{max}$ and was not BQL at 336 h post-dose. Blood concentrations were lower than plasma concentrations for all time points post-dose and did not reach BQL levels at 336 h post-dose. The majority of tissues had $t_{max}$ values at 0.5 h post-dose, but all tissues were not BQL by 336 h post-dose except for the brain (whole) and lens. The majority of tissues had tissue:plasma $AUC_{0-t}$ ratios less than 1.

The [$^{14}$C]-TFS-2-derived radioactivity $C_{max}$ in tissues other than blood ranged from 292 µg equiv/g in the blood (cardiac) to 0.138 µg equiv/g in the lens following an IV (50 mg/kg) dose of [$^{14}$C]-TFS-2 to female SD rats. The majority of peak tissue radioactivity concentrations were observed at 0.5 h after dosing, except for brain (whole), esophagus wall, meninges, nasal turbinates, pancreas, and small intestine wall, which occurred at 1 h; bone (femur), bone marrow (femur), intra-orbital lachrymal gland, and pituitary gland, which occurred at 3 h; cecum mucosa, Harderian gland, liver, thyroid gland, and uveal tract, which occurred at 6 h; large intestine wall, lymph node (cervical), trachea, and vagina, which occurred at 24 h; white fat (inguinal), which occurred at 72 h; and spleen, which occurred at 336 h after dosing.

Conclusion

[$^{14}$C]-TFS-2-related material was quickly and widely distributed throughout the body with the majority of tissues showing the highest concentrations at 1 h for male LE rats and 0.5 h for male and female SD rats after the IV dosing of [$^{14}$C]-TFS-2. The highest concentrations of [$^{14}$C]-TFS-2-derived radioactivity were measured in the lymphatic, metabolic/excretory and vascular systems, as well as the gastrointestinal tract and lung. Regardless of strain or sex, concentrations in the brain (whole), eye, lens, and spinal cord were lower than all other tissues in all other tissue systems. In addition, there was no significant increased distribution of radioactivity to melanin-containing tissues, such as the meninges, uveal tract and pigmented skin, in the LE rats, indicating that [$^{14}$C]-TFS-2-derived radioactivity was not preferentially associating with melanin.

Example 10. Genotoxicity Study

Genotoxicity studies for the polymer excipient will be performed according to "ICH Guidance for Industry S2B Genotoxicity: A Standard Battery for Genotoxicity Testing of Pharmaceuticals" (July 1997). The standard panel of assays include genotoxicity in bacterial reverse mutation test and assessment of DNA damage in mammalian cells (CYP450 assays). The in vivo DNA damage will be assessed during the GLP toxicology study in rats.

Example 11. Bioequivalence Study

This is a phase 1, randomized, multi-center, open-label, parallel group cross-over bioequivalence study to evaluate the safety, tolerability, and pharmacokinetics of intravenously infused TFRP-1 and IXEMPRA® in subjects with metastatic or locally advanced breast cancer. Subjects will be randomized (1:1) into therapeutic groups to be administered either TFRP-1 or IXEMPRA® by intravenous (IV) infusion. Twenty (20) patients with metastatic or locally advanced breast cancer after failure of an anthracycline, a taxane, and capecitabine will be randomized (1:1) to receive monotherapy with either IXEMPRA® or TFRP-1 (10 patient per group). During the first 21-day cycle, Day 1, 10 patients will receive TFRP-1, and another 10 patients will receive IXEMPRA® infusion over 3 hours at a dose of 40 mg/m². During the second 21-day cycle, Day 1, patients will be crossed-over, such that the patients from the IXEMPRA® group will receive TFRP-1, and the patients from the TFRP-1 group will receive IXEMPRA® infusion. After the second infusion of investigation drugs, the patients will be followed for an additional 21 days. A follow-up visit will be performed on the 22nd day after the second infusion.

Subjects will be administered IXEMPRA® and TFRP-1 by a 3-hour IV infusion on Day 1 of Cycle 1 and Cycle 2. Each Cycle will last for 21 days. After the completion of the follow-up visit (Day 22 after the second infusion), i.e., after the end of study participation, the subjects may continue treatment at the treating physician's discretion.

Physical examination (including height (screening only) and body weight) will be performed at screening, prior to dosing on Day 1, Days 2 and 15 (non-dosing days) of Cycle 1, Cycle 2 and at the follow-up visit (4 weeks after the last dose of study drug). Eastern Cooperative Oncology Group (ECOG) performance status will be performed at screening, prior to dosing on Day 1 of Cycle 1, at Day 21 of Cycle 1 and at the follow-up visit. Vital signs (blood pressure, pulse rate, respiration rate, and oral body temperature) will be measured at screening, prior to dosing on Days 1, 8, and 15 of treatment Cycle 1 and Cycle 2, and at the follow-up visit. In addition, on Day 1 of Cycle 1 and Cycle 2, vital signs will be measured at the completion of study drug infusion, and at 5 minutes, 15 minutes, 30 minutes, 1 hour, 2 hours, 4 hours, and 8 hours after the end of the infusion.

Electrocardiograms (ECGs) will be performed at screening, Day 1 and Day 2 of Cycle 1 and Cycle 2 (prior to dosing and one hour after the end of study drug infusion), as well as at the follow-up visit. Chest x-rays will be performed at screening, at the end of two treatment cycles, and at the follow-up visit. Hematology, serum chemistry, and urinalysis will be measured at screening, prior to dosing on Day 1, and on Days 2 and 15 (non-dosing days) of Cycle 1, on Day 15 and Day 21 of Cycle 2, and at the follow-up visit. Blood samples for the evaluation of the PK profile of ixabepilone will be collected prior to dosing on Day 1 of Cycle 1, at the completion of study drug infusion on Day 1 of Cycle 1, and at 15, 30, 45 minutes, and 2, 3, 4, 6, 8, 24, 48, and 72 hours after the end of the infusion on Day 1 of Cycle 1. The same collection schedule will be repeated for Cycle 2.

Subjects 18 years of age or older with histologically or cytologically confirmed metastatic or locally advanced breast cancer after failure of an anthracycline, a taxane and capecitabine will be eligible for the trial, subject to the exclusion criteria described below. Subject must have evaluable or measurable disease.

Subjects meeting any of the following criteria will be excluded from the trial:
1. ECOG performance status >2;
2. Life expectancy <3 months;
3. White blood cell count <3,000/mm³;
4. Absolute nuetrophil count <1,500/mm³;
5. Platelet count <100,000/mm³;
6. Hemoglobin <9.0 g/dL;
7. Bilirubin ≥1.5 mg/dL (regardless of liver metastases);
8. AST and ALT ≥3 times upper limit of normal (ULN) (≥5 times ULN if liver metastases present);
9. Creatinine >1.5 mg/dL or creatinine clearance ≤50 mL/min;
10. Major surgery within 4 weeks prior to screening
11. Positive serology test results for hepatitis B surface antigen, hepatitis C virus antibody, or HIV antibody;
12. Meningeal or CNS metastases or carcinomatous meningitis;
13. Other malignancy within the past 5 years, except adequately treated basal cell or squamous cell skin cancer;
14. Recent history (within 12 months of screening) of major cardiac or neurologic disease including but not limited to angina pectoris, symptomatic coronary artery disease, uncontrolled hypertension (at time of study entry), New York Heart Association (NYHA) Class III or IV congestive heart failure, confirmed significant cardiac conduction abnormalities (including QTc >0.45 sec) or arrhythmias, myocardial infarction, cerebrovascular accidents, or transient ischemic attacks;
15. Signs or symptoms of other major diseases including, but not limited to, end organ failure, major chronic illnesses other than cancer, hemolytic conditions (e.g., sickle cell disease) or active infections which, in the opinion of the investigator, places the subject at unacceptable risk if he/she were to participate in the study;
16. Pregnant or breast-feeding;
17. Other anti-cancer therapy (chemotherapy, radiotherapy, or immunotherapy) within 3 weeks of screening;
18. Other investigational drug within 30 days of screening;
19. Not recovered from other anti-cancer treatment or investigational drug [i.e., ≥Grade 2 AEs, except for alopecia (any grade is acceptable) and fatigue (Grade 2 is acceptable)];
20. Known allergy to the active or inactive ingredients of the study drug.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A composition comprising ixabepilone, or a pharmaceutically acceptable salt thereof, and a copolymer represented by formula I:

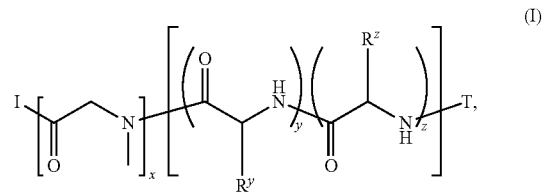

wherein:
I is an initiating group;
T is a terminal group;
$R^y$ and $R^z$ are each independently an amino acid side chain, wherein $R^y$, taken together with the amino acid backbone to which it is attached, forms a D-amino acid and $R^z$, taken together with the amino acid backbone to which it is attached, forms an L-amino acid wherein $R^y$, taken together with the amino acid backbone to which it is attached, forms leucine, and wherein $R^z$, taken together with the amino acid backbone to which it is attached, forms tyrosine;
x is an integer from 125 to 350;
y is an integer from 5 to 35; and
z is an integer from 5 to 35.

2. The composition of claim 1, wherein the copolymer is represented by formula II:

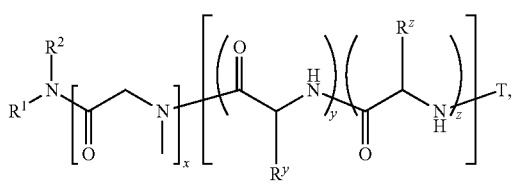

(II)

wherein:
R[1] and R[2] are each independently hydrogen or optionally substituted (C$_1$-C$_{10}$)aliphatic.

3. The composition of claim 2, wherein R[1] is hydrogen and R[2] is optionally substituted (C$_1$-C$_{10}$)aliphatic.
4. The composition of claim 1, wherein T is hydrogen.
5. The composition of claim 1, wherein T is optionally substituted aliphatic.
6. The composition of claim 1, wherein T is an acyl group.
7. The composition of claim 1, wherein x is 175.
8. The composition of claim 1, wherein y is an integer from 25 to 35.
9. The composition of claim 1, wherein z is an integer from 16 to 30.
10. The composition of claim 1, wherein y is 30 and z is 20.
11. The composition of claim 1, wherein the copolymer is represented by formula III:

(III)

12. The composition of claim 1, wherein the copolymer is represented by formula IV:

(IV)

13. The composition of claim 1, wherein the composition is in the form of mixed micelles.
14. The composition of claim 1, comprising from about 5% to about 15% ixabepilone, or a pharmaceutically acceptable salt thereof, by weight.
15. The composition of claim 1, comprising from about 40% to about 50% copolymer by weight.
16. A composition comprising:
   about 10% ixabepilone by weight;
   about 45% copolymer by weight; and
   about 45% glycine by weight,
   wherein the copolymer is represented by the following structural formula:

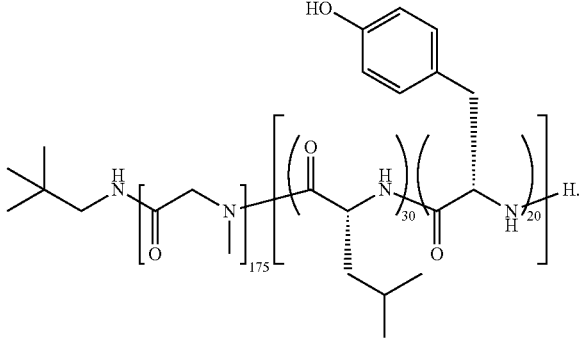

17. A unit dose form of a composition comprising:
   about 20 mg ixabepilone;
   about 180 mg copolymer; and
   about 180 mg glycine,
   wherein the copolymer is represented by the following structural formula:

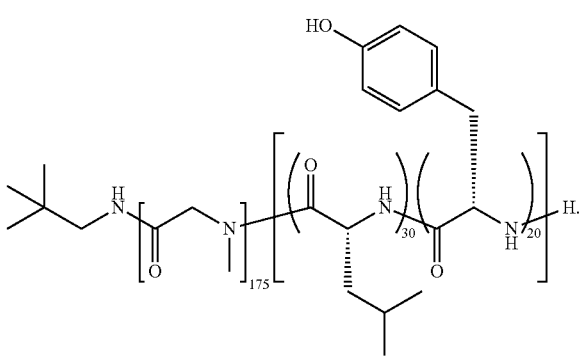

18. A method for treating cancer in a subject in need thereof, comprising administering to the subject an effective amount of a composition of claim 1.
19. The method of claim 18, wherein the cancer is breast cancer, bladder cancer, pancreatic cancer, prostate cancer, non-small cell lung cancer or colorectal cancer.
20. The method of claim 19, wherein the cancer is breast cancer.
21. The method of claim 20, wherein the cancer is metastatic or locally advanced.
22. The method of claim 18, further comprising administering to the subject one or more additional therapeutic agents.
23. A method of preparing a composition of claim 1, comprising:
   a) dissolving ixabepilone, or a pharmaceutically acceptable salt thereof, the copolymer and, optionally, a cryoprotectant in aqueous tert-butanol, thereby forming a mixed solution; and
   b) lyophilizing the mixed solution, thereby preparing the composition.

* * * * *